US005827237A

United States Patent [19]
Macoviak et al.

[11] Patent Number: 5,827,237
[45] Date of Patent: Oct. 27, 1998

[54] DUAL LUMEN CATHETER WITH CONTROLLED ANTEGRADE AND RETROGRADE FLUID FLOW

[75] Inventors: John A. Macoviak, Huntington Beach; Michael Ross, Hillsborough, both of Calif.

[73] Assignee: Cardeon Corporation, Saratoga, Calif.

[21] Appl. No.: 664,361

[22] Filed: Jun. 17, 1996

[51] Int. Cl.$^6$ ..................................................... A61M 5/00
[52] U.S. Cl. ........................... 604/246; 604/96; 604/249; 604/280
[58] Field of Search ................................ 604/33, 280, 96, 604/249, 93, 264, 248, 53, 104–109, 246; 128/658; 600/18

[56] References Cited

U.S. PATENT DOCUMENTS

| | | |
|---|---|---|
| 3,592,184 | 7/1971 | Watkins et al. ........................ 128/1 R |
| 3,769,983 | 11/1973 | Meran ..................................... 128/351 |
| 3,995,617 | 12/1976 | Watkins et al. . | |
| 4,056,854 | 11/1977 | Boretos et al. . | |
| 4,407,271 | 10/1983 | Schiff ........................................ 128/1 |
| 4,785,795 | 11/1988 | Singh . | |

FOREIGN PATENT DOCUMENTS 3607 295 A1  9/1987  Germany .

Primary Examiner—Corrine M. McDermott
Assistant Examiner—Cris L. Rodriguez
Attorney, Agent, or Firm—Fulwider Patton Lee & Utecht, LLP

[57] ABSTRACT

A catheter device regulates fluid flow within a circulatory vessel. Included is an elongated catheter body configured to access one of a circulatory vessel or a heart chamber. The catheter body includes a proximal end, a distal end, and a first lumen including an open proximal end and a distal end with a port formed at a distal portion of the distal end. A second lumen is also included in the catheter body with an open proximal end. An antegrade valve is coupled to an exterior of the catheter body and configured to provide a controllable antegrade flow and a controllable retrograde flow along the exterior of the catheter body. The antegrade flow is greater than the retrograde flow. A retrograde valve may be included which provides a controllable retrograde and antegrade flow along the exterior of the catheter body. When a retrograde valve is used, the retrograde flow is greater than the antegrade flow.

29 Claims, 19 Drawing Sheets

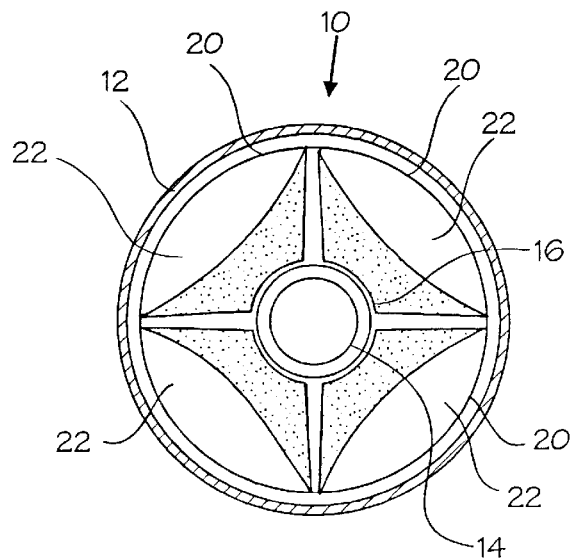
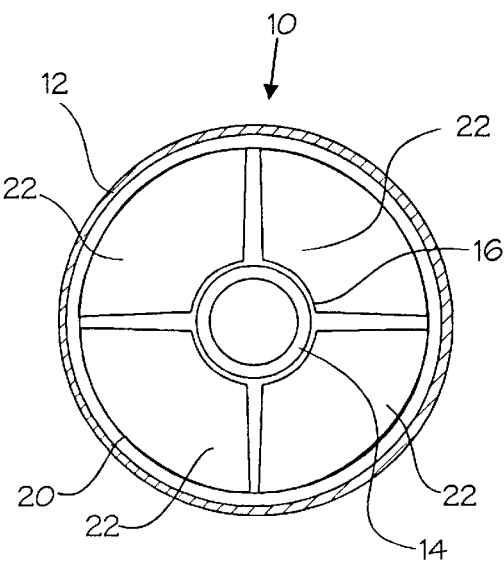
Fig. 1(a)                Fig. 1(b)
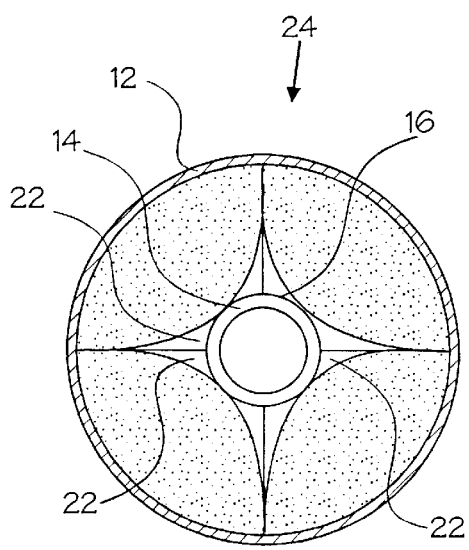
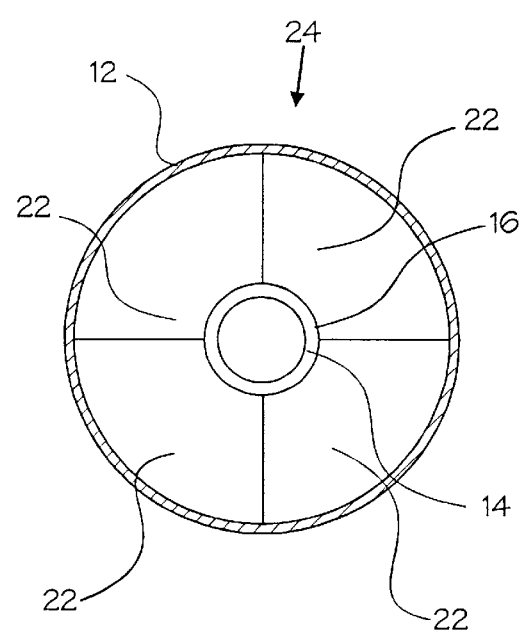
Fig. 2(a)                Fig. 2(b)

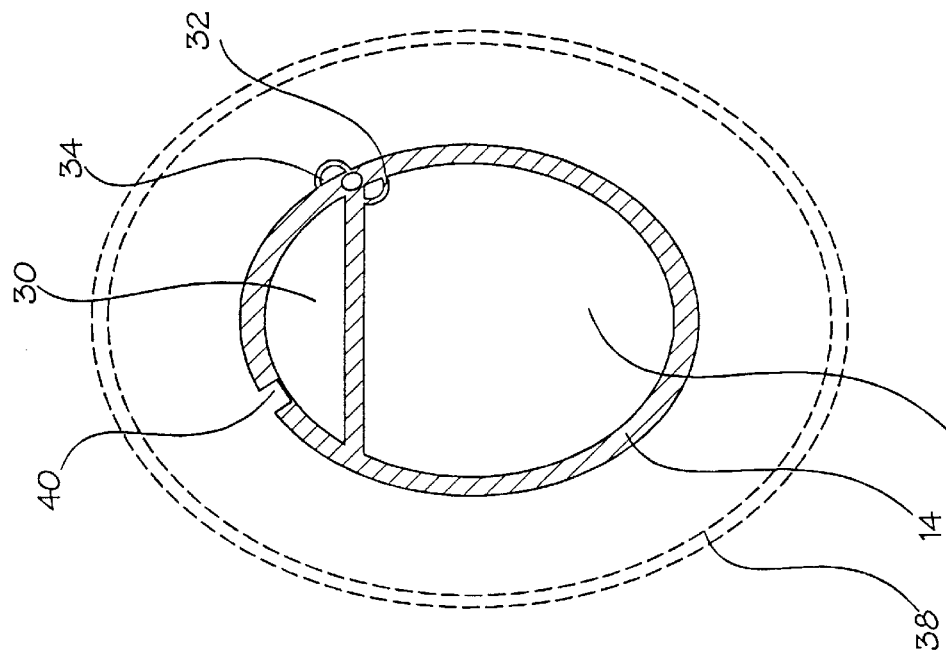
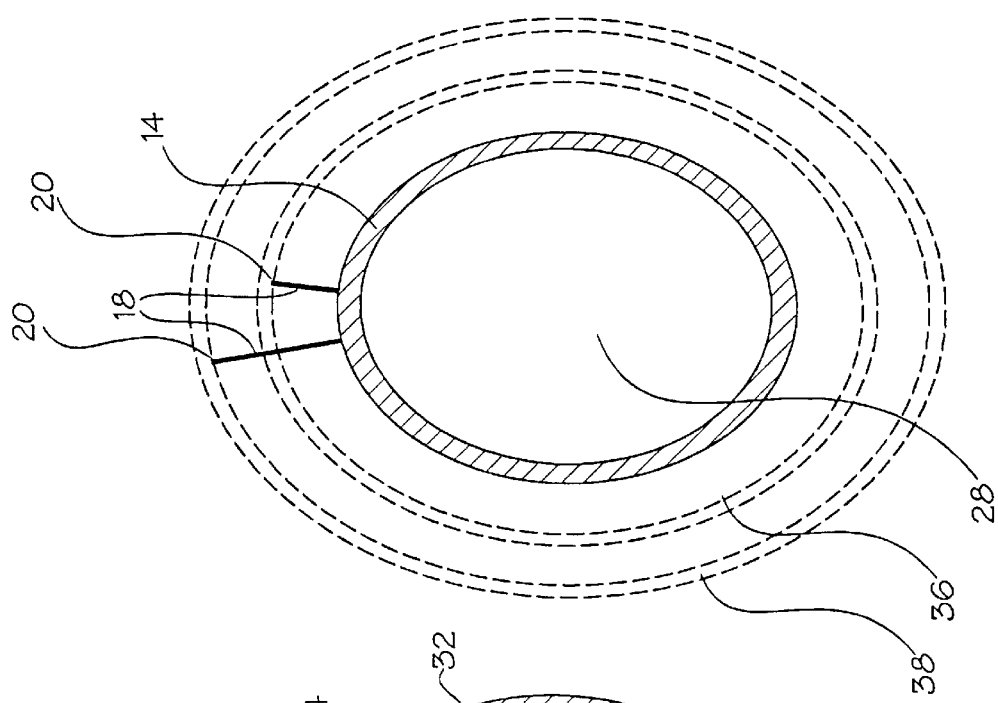
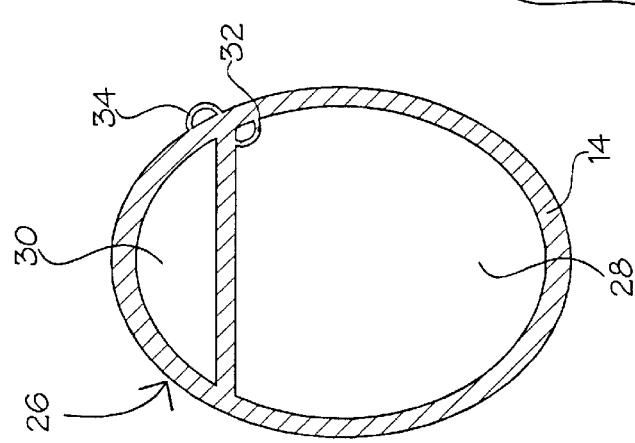

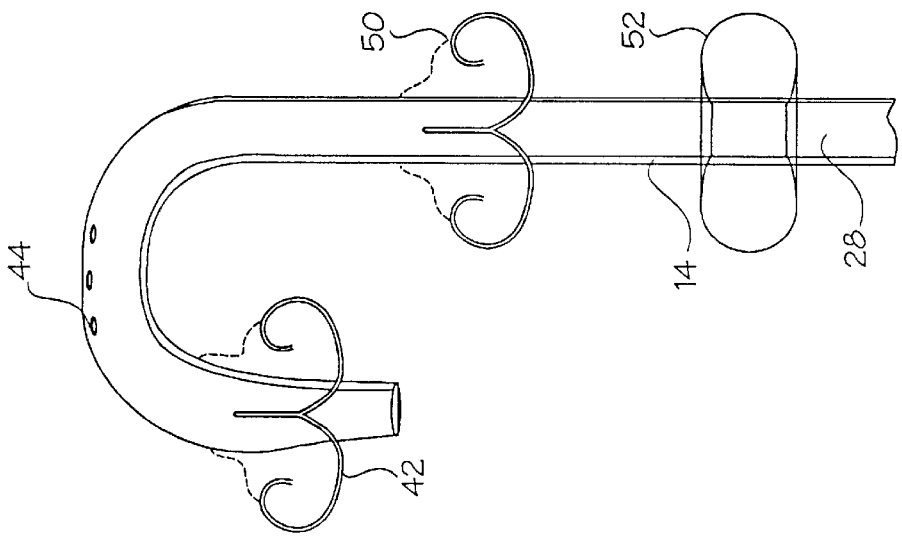
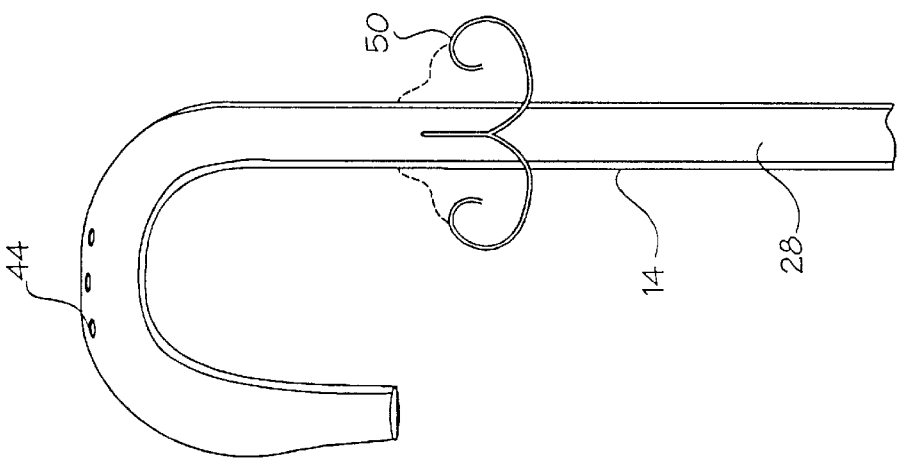
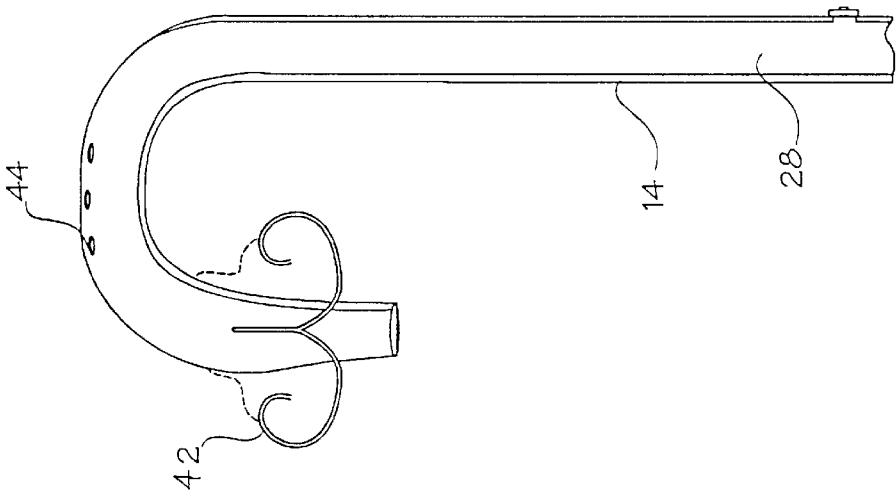

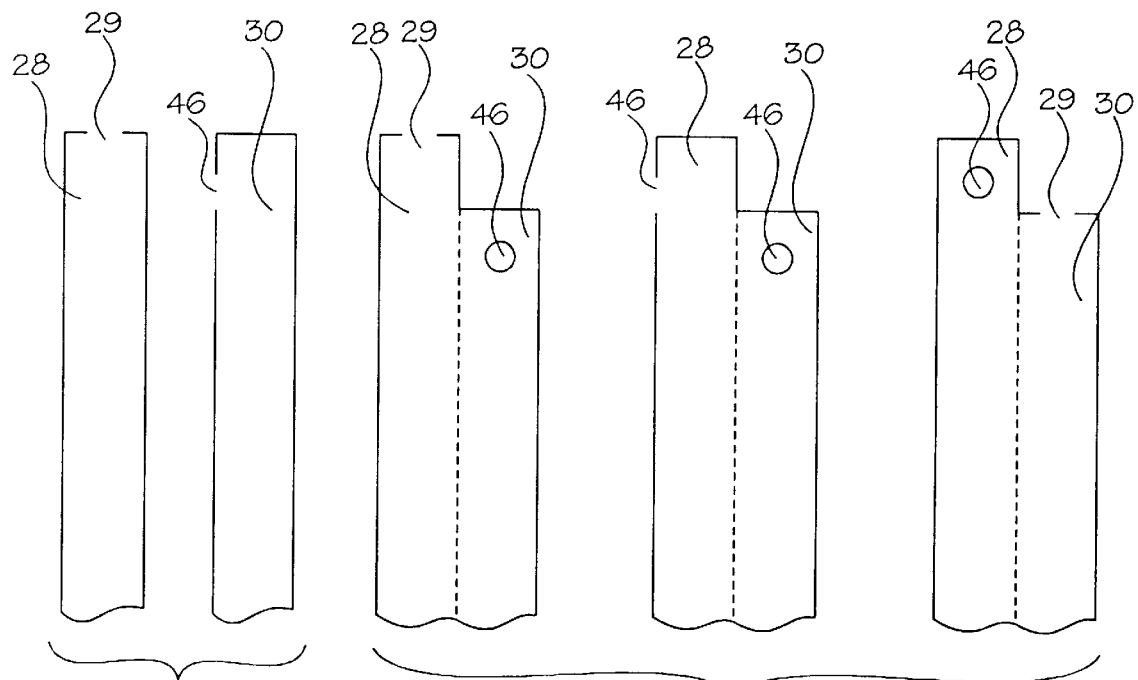
Fig. 26(b)
Fig. 26(c)
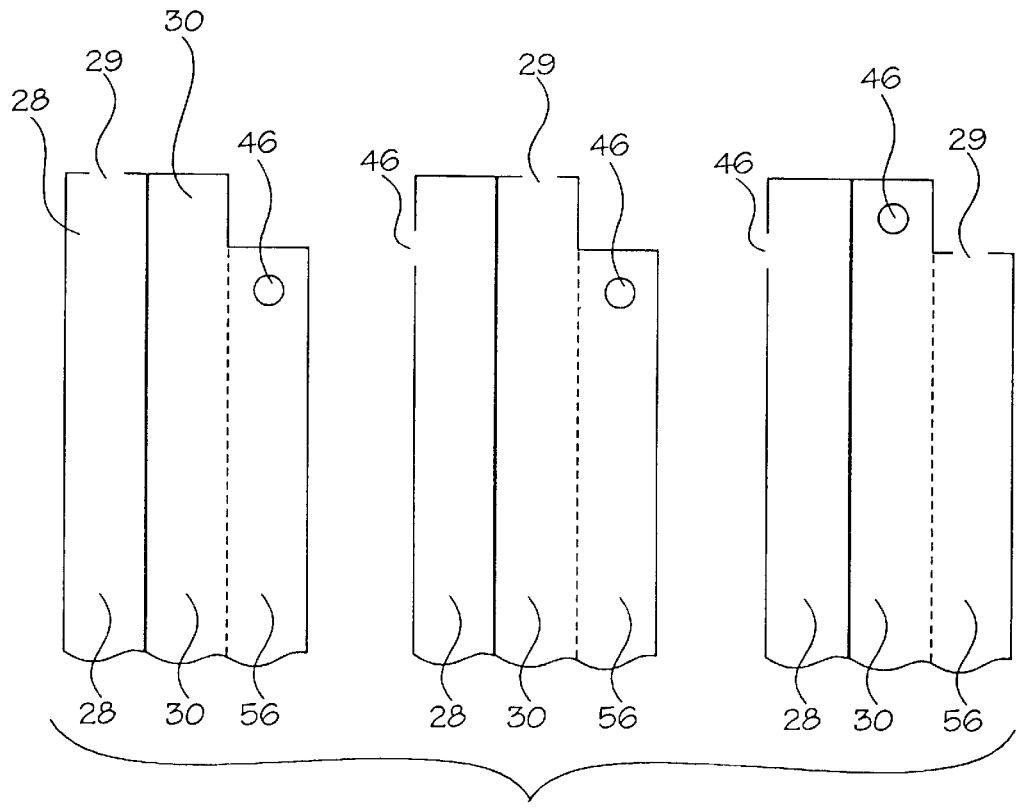
Fig. 26(d)

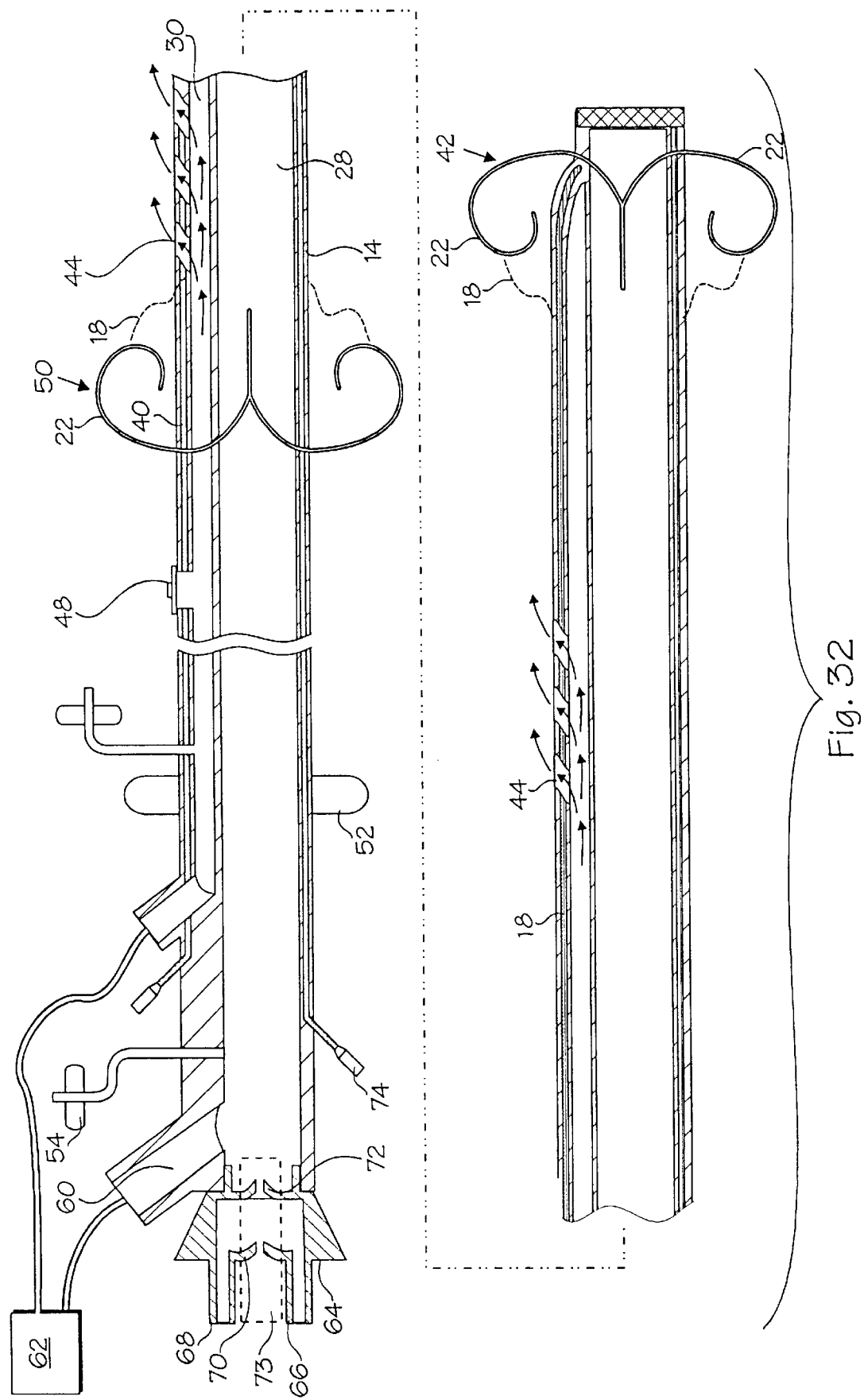

DUAL LUMEN CATHETER WITH CONTROLLED ANTEGRADE AND RETROGRADE FLUID FLOW

BACKGROUND OF THE INVENTION

1. Field of the Invention

This invention relates generally to a catheter to regulate fluid flow through and around the catheter, and more particularly to a catheter which includes at least one antegrade valve coupled to an exterior of the catheter and configured to provide a controlled antegrade flow and a controlled retrograde flow past an exterior of the catheter within the circulatory vessel and/or a catheter which includes at least a retrograde valve coupled to the exterior of the catheter configured to provide a controlled antegrade flow and a controlled retrograde flow.

2. Description of Related Art

Various cardiovascular, neurosurgical, pulmonary and other interventional procedures, including repair or replacement of aortic, mitral and other heart valves, repair of septal defects, pulmonary thrombectomy, coronary artery bypass grafting, angioplasty, atherectomy, treatment of aneurysms, electrophysiological mapping and ablation, and neurovascular procedures, are performed with the patient connected to cardiopulmonary bypass (CPB) equipment to maintain circulation of oxygenated blood throughout the patient's circulatory system. In some of these procedures, such as heart valve replacement and coronary artery bypass grafting, cardiac function is arrested, and peripheral circulation of oxygenated blood is maintained completely by a CPB system. In other procedures, such as angioplasty and atherectomy, the heart remains beating, and CPB is used to assist the heart in maintaining circulation of oxygenated blood during the procedure.

To establish cardiopulmonary bypass according to conventional techniques, a venous cannula is introduced into a major vein such as the inferior vena cava, or into the heart itself, to withdraw deoxygenated blood from the patient and deliver the deoxygenated blood to a CPB system for oxygenation. An arterial cannula is introduced into a major artery such as the aorta, an iliac artery, or a femoral artery, for delivering oxygenated blood from the CPB system to the patient's arterial system.

For endovascular procedures such as angioplasty and atherectomy in which cardiac function need not be arrested, interventional devices are introduced into an artery such as a femoral artery, and the devices are transluminally positioned at the treatment site where the procedure is performed. For example, in angioplasty or atherectomy, a catheter is introduced into a femoral artery and advanced through the aorta into a coronary artery to treat an occluded region therein. If CPB is utilized during such procedures, the arterial and venous CPB cannulae are usually introduced into a femoral artery and femoral vein, respectively, by means of a surgical cut-down or over guide wires percutaneously placed in the groin area on one side of a patient's body. Interventional devices may then be introduced into a femoral artery or vein in the groin area on the other side of the patient's body.

In procedures where cardiac function is arrested, on the other hand, the heart and coronary arteries must be isolated from the remainder of the patient's arterial system. Using conventional techniques, the sternum is cut longitudinally (a median sternotomy), providing access between opposing halves of the anterior portion of the rib cage to the heart and other thoracic vessels and organs. Alternatively, a lateral thoracotomy is formed, wherein an incision, typically 10 cm to 20 cm in length, is made between two ribs. A portion of one or more ribs may be permanently removed to optimize access. Through this large opening in the chest, a mechanical cross-clamp may be placed externally on the ascending aorta downstream of the ostia of the coronary arteries, but upstream of the brachiecephalic artery, so as to allow oxygenated blood from the CPB system to reach the arms, neck, head, and remainder of the body. A catheter is then introduced through the sternotomy or thoracotomy and inserted into the ascending aorta between the cross-clamp and the aortic valve. Cardioplegic fluid is infused through the catheter into the aortic root and coronary arteries to perfuse the myocardium. An additional catheter may be introduced into the coronary sinus for retrograde perfusion of the myocardium with cardioplegic fluid. In addition, the myocardium is usually cooled by irrigation with cold saline solution and/or application of ice or cold packs to the myocardial tissue. Cardiac contractions will then cease.

While such open-chest techniques can produce significant benefits for some patients, such techniques entail many days to weeks of hospitalization and months of recuperation time, in addition to the pain and trauma suffered by the patient. Moreover, application of an external cross-clamp to a calcified or atheromatous aorta may cause the release of emboli into the brachycephalic, carotid or subclavian arteries with serious consequences such as strokes.

In response to these problems, new techniques have been developed to facilitate the performance of cardiac procedures such as heart valve repair, coronary artery bypass through a small incision and replacement using endovascular instruments, eliminating the need for a thoracotomy as well as the need for an external aortic cross-clamp. Such procedures are described in co-pending application Ser. No. 07/991,188 and application Ser. No. 07/730,559, which are assigned to the assignee of the present invention and are incorporated herein by reference. Similarly, in commonly-assigned U.S. patent application Ser. No. 08/023,778, the complete disclosure of which is incorporated herein by reference, methods and devices are described for performing coronary artery bypass grafting and other procedures through small incisions or cannulae positioned through the chest wall, obviating the need for a thoracotomy. This new generation of minimally-invasive cardiac procedures provides significant advantages over conventional open surgical techniques, including reduced mortality and morbidity, decreased patient suffering, reduced hospitalization and recovery time, and lowered medical costs relative to open-chest procedures.

These new generation minimally-invasive cardiac procedures and devices use balloons to isolate vessels and different sections of the heart. These balloons require large fluid inflation lumens in the catheter, thereby diminishing respective effective inner diameters or requiring larger catheters. When the balloon is large the wall tensions of the balloon are increased and there is a significant chance of balloon rupture. Balloons may disrupt interior lesions of vessels. Additionally, balloons serve as total roadblocks to the passage of fluids, including but not limited to blood.

It would be desirable to provide a catheter configured to access a vein, artery, a great artery or a heart chamber, which uses valves instead of balloons and minimizes the problems associated with balloons. To regulate flow around the catheter it would be further desirable to provide a catheter with exterior antegrade valves that provide antegrade flow past the antegrade valve and a controllable retrograde flow past the antegrade valve. It would be even further desirable to provide exterior retrograde valves that provide retrograde flow past the retrograde valve and a controllable antegrade flow past the retrograde valve.

SUMMARY OF THE INVENTION

Accordingly, an object of the invention is to provide a catheter device configured for access to a patient's vein, artery, heart chamber or a great vessel of the heart.

Another object of the invention is to provide a catheter device configured for access to a patient's vein, artery, heart chamber or a great vessel which includes at least one antegrade valve positioned at an exterior of the catheter body.

A further object of the invention is to provide a catheter device configured for access to a patient's vein, artery, heart chamber or a great vessel which includes at least one retrograde valve positioned at an exterior of the catheter body.

Yet another object of the invention is to provide a catheter device configured for access to a patient's vein, artery, heart chamber or a great vessel which includes at least one antegrade valve and one retrograde valve, both positioned at an exterior of a catheter body.

Still another object of the invention is to provide an antegrade or retrograde valve which is a central flow valve configured to provide a fluid flow through a center portion of the central flow valve whereby fluid flow traverses between the central flow valve and the catheter body.

Another object of the invention is to provide an antegrade or retrograde valve which is a peripheral flow valve configured to provide the antegrade flow around an exterior of the leaflets and traverse between the leaflets and a circulatory vessel wall.

Yet a further object of the invention is to provide a catheter system with an antegrade valve positioned between the coronary ostia and the brachiocephalic artery, a first retrograde valve positioned in the aorta downstream from the antegrade valve, and a second retrograde valve positioned downstream from the first retrograde valve.

Another object of the invention is to provide a catheter system with an antegrade valve positioned between the coronary ostia and the brachiocephalic artery, a first retrograde valve positioned downstream from the first retrograde valve, a second retrograde valve positioned downstream from the first retrograde valve, and a third retrograde valve positioned downstream from the second retrograde valve.

Yet another object of the invention is to provide a catheter system with a first antegrade valve positioned downstream from a pulmonic valve within a pulmonary artery, and a second antegrade valve positioned upstream from the pulmonic valve within one of a right heart chamber or one of a vessel of a venous blood system.

Still another object of the invention is to provide a catheter system with a first antegrade valve positioned downstream from a pulmonic valve within a pulmonary artery, a second antegrade valve positioned upstream from the pulmonic valve within one of a right heart chamber or one of a vessel of a venous blood system, and a first retrograde valve positioned upstream from the pulmonic valve within one of a right heart chamber, a pulmonary vessel or a vessel in a venous blood system.

These and other objects are attained in a catheter device that regulates fluid flow within a circulatory vessel. Included is an elongated catheter body configured to access one of a circulatory vessel or a heart chamber. The catheter body includes a proximal end, a distal end, a first lumen including an open proximal end and a distal end with a port formed at a distal portion of the distal end and a second lumen with an open proximal end. An antegrade valve is coupled to an exterior of the catheter body and configured to provide a controllable antegrade flow and a controllable retrograde flow along the exterior of the catheter body. The antegrade flow is greater than the retrograde flow.

In another embodiment, a retrograde valve is coupled to an exterior of the catheter body. The retrograde valve is configured to provide a controllable retrograde flow and a controllable antegrade flow past the exterior of the catheter body.

The antegrade and retrograde valves can be, (i) a central flow valve configured to provide a fluid flow through a center portion of the central flow valve whereby fluid flow traverses between the central flow valve and the catheter body or (ii) a peripheral flow valve configured to provide the antegrade flow around an exterior of the leaflets and traverse the leaflets and a circulatory vessel wall.

In other embodiments, the catheter body can include one or more antegrade and retrograde valves, as well as one or inflatable balloons.

The antegrade and retrograde valves can be configured to be coupled in a moveable relationship to the exterior of the catheter. The antegrade and retrograde valves can be made of one or more leaflets. In resting positions, the antegrade and retrograde valves are in contacting or adjacent positions with an interior surface of a vessel or heart chamber. Each antegrade or retrograde valve is retractable to provide blood flow in both the antegrade and retrograde directions. One or more advancement and retraction members are coupled to the antegrade and retrograde valves. The advancement and retraction members can be positioned in open ended tracks formed in the catheter body.

The antegrade and retrograde valves are autoregulating in response to differing fluid pressures in the blood stream on either side of the valve so that excessive pressure on the vessel wall is avoided. Additionally, damage to the interiors of vessels and heart chambers is decreased and the chance of a disruption of lesions in the vessels is reduced. Further, the antegrade and retrograde valves are suitable for a variety of different applications, including but not limited to, perfusion, drainage, unidirectional direct flow, controllable unidirectional direct flow, regulation of the amount of flow and the like. Further, unlike balloons which are more subject to bursting, the antegrade and retrograde valves are more robust.

BRIEF DESCRIPTION OF THE FIGURES

FIG. 1(a) is a cross-sectional view of an antegrade central flow valve, illustrating blood flow.

FIG. 1(b) is a cross-sectional view of a retrograde central flow valve, illustrating blood flow.

FIG. 2(a) is a cross-sectional view of an antegrade peripheral flow valve, illustrating blood flow.

FIG. 2(b) is a cross-sectional view of a retrograde peripheral flow valve, illustrating blood flow.

FIG. 3 is a cross-sectional view of a dual lumen catheter.

FIG. 4 is a cross-sectional view of a single lumen catheter with two valves configured for attachment to an exterior surface of the single lumen catheter, where the valves can be antegrade, retrograde, or a combination.

FIG. 5 is a cross-sectional view of a dual lumen catheter with an antegrade or retrograde valve, first and second channels and a track formed in an exterior surface of the dual lumen catheter.

FIG. 9 is a cross-sectional view of a single lumen catheter with an antegrade valve.

FIG. 10 is a cross-sectional view of a single lumen catheter with a retrograde valve.

FIG. 11 is a cross-sectional view of a single lumen catheter with an antegrade valve and a retrograde valve and a retrograde valve.

FIG. 26 (a) is a cross-sectional view of the triple lumen catheter of FIG. 26 taken along the lines 26 (a)—26(a).

FIGS. 26 (b) through 26(d) illustrate different cross-sectional views of double and triple lumen catheters.

FIG. 32 is a cross-sectional view of a dual lumen catheter with a dual diaphragm device coupled to a proximal end of the dual lumen catheter.

DETAILED DESCRIPTION

Figure 1:
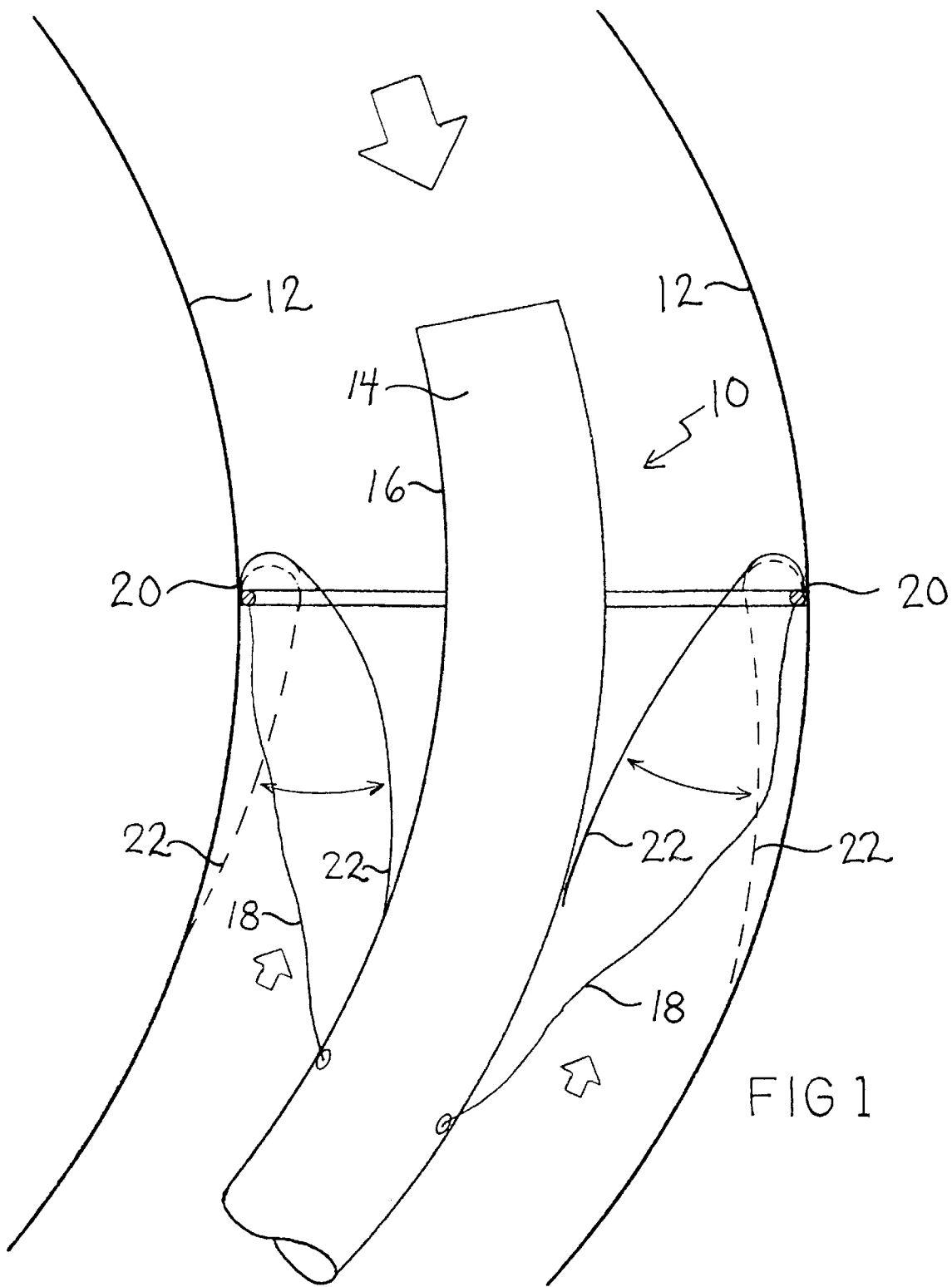
FIG. 1 is a view of an antegrade or retrograde central flow valve.

The present invention is a catheter device that regulates fluid flow within a circulatory vessel by controlling flows through and around a catheter. Included is an elongated catheter body configured to access one of a circulatory vessel or a heart chamber. The catheter body includes a proximal end, a distal end, and a first lumen including an open proximal end and a distal end with a port formed at a distal portion of the distal end. An antegrade valve is coupled to an exterior of the catheter body and configured to provide a controllable antegrade flow and a controllable retrograde flow along the exterior of the catheter body. The antegrade flow is greater than the retrograde flow. In other embodiments, second and third lumens are included. The proximal ends of the second and third lumens are open. The distal ends of the second and third lumens can be open or closed with or without side ports. Distal portions of the second and third lumens can include side ports, which may provide directional fluid flow. One or more antegrade and retrograde valves can be included with a catheter body. Further, one or more balloons may also be included, along with their associated elongated catheter inflation lumens.

The elongated catheter body or cannula of the catheter device is indicated generally throughout the patent specification and drawings by the reference number 14. The terms "catheter" and "cannula" are generally synonymous in the art and will be used interchangeably within the specification to refer to the elongated catheter body 14. The various illustrative embodiments of the catheter device will be referred to by their respective figure numbers and will be differentiated from one another by the number, size and function of the lumens within the elongated catheter body 14 and the number, type and location of the valves and/or balloons along the elongated catheter body 14.

Each antegrade or retrograde valve can be a central blood flow valve or a peripheral flow valve and made of one, two, three or more leaflets. The leaflets can include one or more fenestrations. The fenestrations may be longitudinal slits which provide for one-way flow. Antegrade and retrograde valves are either central flow or peripheral flow valves.

For purposes of the present application, "downstream" means in the direction of normal blood flow through a blood vessel, i.e., further from the heart in the arterial system, and closer to the heart in the venous system. "Upstream" means in the direction opposite the downstream direction. With respect to devices, "proximal" means in the direction toward the end of the device that is closest to and held or manipulated by the user, while "distal" means in the direction away from the user, opposite the proximal direction. "Antegrade flow" means fluid or blood flow in the direction of normal circulation. "Retrograde flow" means fluid or blood flow in the opposite direction to normal blood circulation.

"Controllable antegrade flow" and "controllable retrograde flow" mean that the flow around an exterior of the catheter body flows primarily in one direction or the other, and the level of flow is determined based upon the construction of the antegrade or retrograde valve. With an antegrade valve, there is more flow in the antegrade direction than in the retrograde direction. With a retrograde valve, there is more flow in the retrograde direction than in the antegrade direction. The difference in flow is dependent on the construction of the valve and may be as little as a few percent to a much greater percentage.

A central flow valve 10, illustrated in FIGS. 1, 1(a) and 1(b), is positioned in a circulatory vessel 12. As illustrated, central flow valve 10 is coupled to a catheter 14 at an exterior 16 of catheter 14. An advancement and retraction member 18 is coupled to a distal portion of catheter 14 at an attachment point 20. Advancement and retraction member 18 is made of a variety of different materials including but not limited to a shaped memory metal, stainless steel and the like. Attachment point 20 can be a hinge point, and is generally at the distal end of a leaflet 22.

Catheter 14 has a diameter suitable for introduction through a femoral or iliac artery, usually less than about 9 mm. The length of catheter 14 is preferably greater than about 80 cm, usually about 90–100 cm, with its proximal end disposed outside of the body, preferably from the femoral or iliac artery in the groin area. Alternatively, catheter 14 may be configured for introduction through the carotid artery, through the brachial artery, or through a penetration in the aorta itself, wherein catheter 14 may have a length in the range of 20 to 60 cm.

Catheter 14 may be constructed of any of a variety of materials, including biocompatible polymers such as polyurethane, polyvinyl chloride, polyether block amide, or polyethylene. In one embodiment, catheter 14 is made of urethane with a shore durometer in the range of 50 D–80 D. Catheter 14 may have a bending modulus in the range of 70 to 100 kpsi, preferably about 80–90 kpsi. A bending modulus in this range provides sufficient stiffness to optimize pushability from a femoral or iliac artery to the ascending aorta, while providing sufficient flexibility to navigate the tortuous iliac artery and the aortic arch.

Leaflets 22 may have curved distal ends with a curved rim that is proximal to a distal end of leaflets 22. Leaflets 22 may be formed of the same material as catheter 14. In their resting position, leaflets are positioned in a direction adjacent to or against a wall of circulatory vessel 12. Leaflets 22 have generally smooth surfaces and collectively are configured to impede fluid flow in their resting position. In the resting position, leaflets 22 are configured to overlap, be closely positioned relative to each other in order to eliminate fluid flow gaps.

When blood flow is in the antegrade direction, the blood flow displaces leaflets 22 away from catheter 14 towards a wall of circulatory vessel 12. When retrograde flow is encountered, central flow antegrade valve 10 directs the flow back into a cusp area, defined by leaflets 22, bringing leaflets 22 back towards the center to close off the retrograde flow.

In the retrograde direction, blood fills the bottom or a low point of central flow valve 10 at a cusp. This causes central flow valve 10 to snap up against the exterior of catheter 14 and/or together so that no retrograde flow goes between leaflets 22 and catheter 14.

Fluid flow in the antegrade direction is between leaflets 22. Retrograde fluid flow pushes leaflets 22 together at a central point.

Figure 2:
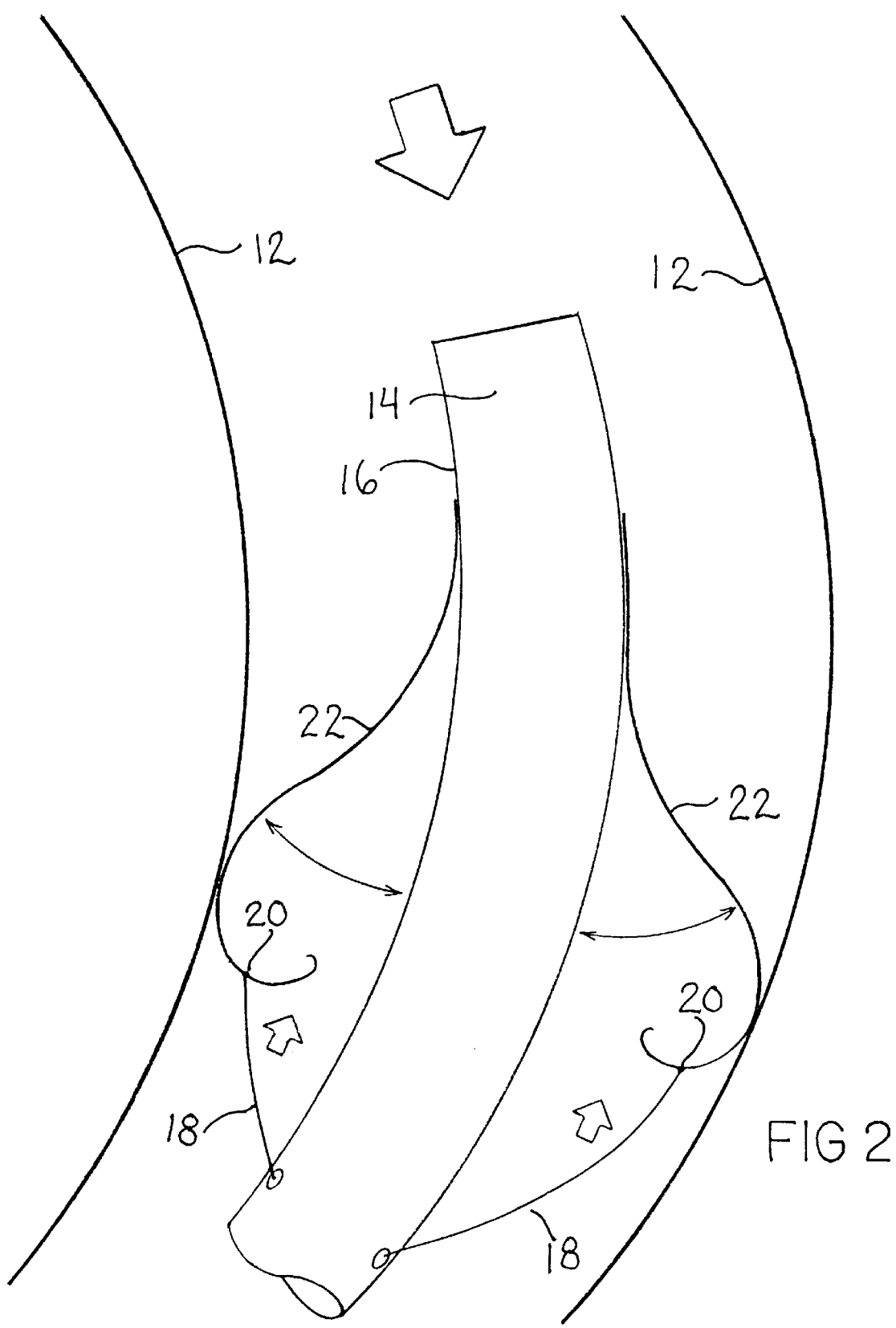
FIG. 2 is a view of an antegrade or retrograde peripheral flow valve.

FIGS. 2, 2(a) and 2(b) illustrate a peripheral flow valve 24. Peripheral flow valve 24 is comprised of one, two, three or more leaflets 22. Advancement and retraction member 18 is coupled to a surface of a leaflet 22. In the retrograde direction, fluid flow encounters peripheral flow valve 24, and pushes leaflets 22 out towards a wall of circulatory vessel 12. With peripheral blood flow valve 24 fluid flow is around the outside of leaflets 22, between the wall of circulatory vessel 12 and an outer wall of valve leaflets 22. The retrograde flow pushes leaflets 22 up against the wall of circulatory vessel 12.

Retrograde fluid flow "puffs" central flow valve 10 and peripheral flow valve 24. With central flow valve 10, retrograde fluid flow puffs the central flow valve 10 in a downward direction and narrows a central fluid passage. With peripheral flow valve 24, retrograde fluid flow pushes leaflets 22, fills the cusps defined by leaflets 22 and advances leaflets 22 towards and against a wall of circulatory vessel 12, preventing peripheral blood flow around the peripheral flow valve 24.

With peripheral flow valve 24, antegrade fluid flow is allowed by pushing leaflets 22 in from the interior wall of circulatory vessel 12 towards catheter 14, permitting blood flow to go around the outside of leaflets 22. In the retrograde direction, blood flow fills the cusps and pushes leaflets 22 out against the wall of circulatory vessel 12.

Catheter 14 can include one or more lumens. FIG. 3 illustrates a cross-section view of a double lumen antegrade or retrograde double lumen cannula 26 including a first lumen 28, and a second lumen 30. As shown first lumen 28 is larger than second lumen 30. Each lumen is configured to be a fluid flow, e.g. blood flow lumen, or adapted to receive a variety of different implements, including but not limited to working tools, scopes, irrigation and aspiration lumens, cardioplegia introduction lumens and the like. A first track 32 and a second track 34 are each configured for receiving advancement and retraction member 18, a balloon inflation and deflation medium, working tools and the like. First track 32 is positioned in an interior of first lumen 28, while second track 34 is positioned at an exterior surface of catheter 14. Additionally, a channel can be positioned within an interior wall defining catheter 14. When a channel is located within an interior wall defining catheter 14, there is a saving of valuable space. The same is true when a channel is positioned at an exterior of catheter 14. In both instances, the available volume for first and second lumens 28 and 30 is maximized.

FIG. 4 depicts cannula 14 with only first lumen 32, and includes a first antegrade or retrograde valve 36 and a second antegrade or retrograde valve 38, each positioned in a fixed or slidable relationship to the exterior of cannula 14. Valves 36 and 38 have free-edges shown in their resting positions, and the associated advancement and retraction members 18 are relaxed. Also shown are attachment points 20 of advancement and retraction members 18 when valves 36 and 38 are in their resting positions.

In FIG. 5, catheter 14 includes first lumen 28 second lumen 30, antegrade or retrograde valve 38, first track 32, second track 34 and a third track 40 that includes an open section. Third track 40 can be used to receive advancement and retraction member 18, a scope, an irrigation or aspiration lumen, working tools, and the like. In one embodiment, a diaphragm device within valve leaflets 22 or equivalent structure is coupled to third track 40 to allow devices to pass through valve leaflets 22. At a proximal end of third track 40 the diaphragm device provides for the passage of an instrument but eliminates blood or other fluid leakage.

Figure 6:
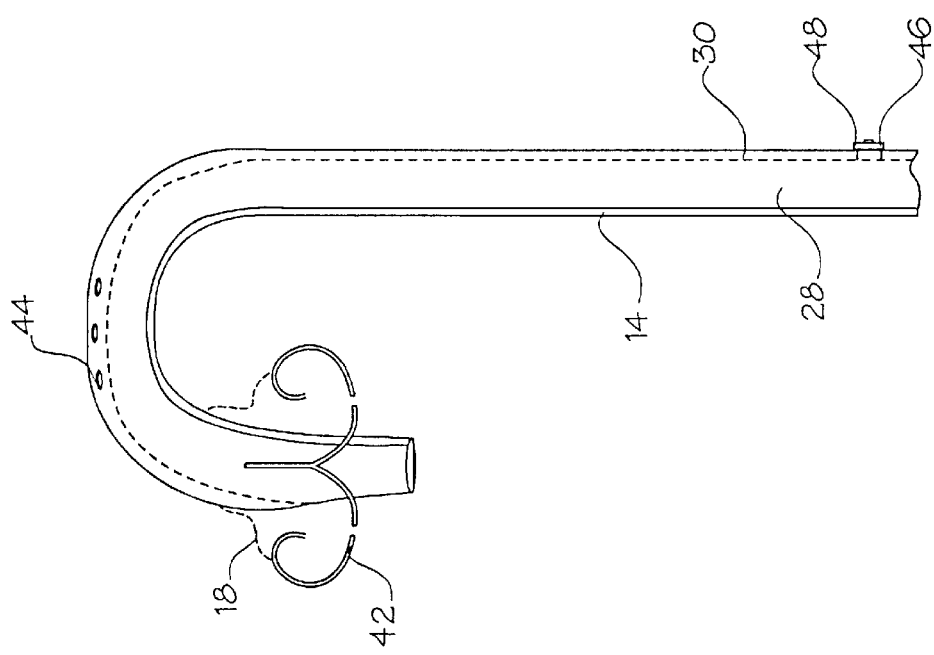
FIG. 6 is a cross-sectional view of a dual lumen catheter with an antegrade valve.

Referring now to FIG. 6, double lumen cannula 14 includes an antegrade valve 40 positioned at a distal portion of double lumen cannula 14. Directional side ports 44 are formed in double lumen cannula 14 and in second lumen 30. Directional side ports 44 are downstream from the distal end of first lumen 28 and downstream from antegrade valve 42. In one embodiment shown in FIG. 24, directional side ports 44 are configured to provide a downstream directional fluid or blood flow, as illustrated by the arrows. A side port 46 is formed in first lumen 28 or second lumen 30 and permits flow of a fluid to and from the respective lumen 28 or 30. A slidable member 48 is configured to advanced and retracted along the exterior of catheter 14 (single or double lumen), and is coupled to an advancement and retraction member 18 in order to open or close side port 46 and permit fluid or blood flow to come out of first or second lumens 28 or 30. Fluid flow in the circulatory vessel is upstream or downstream depending on the position of slidable member 48.

Figure 8:
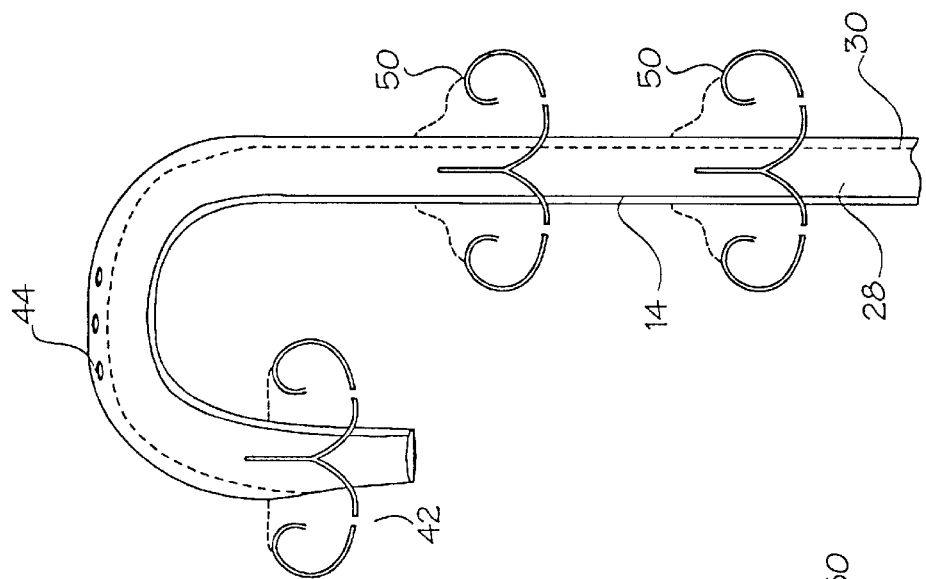
FIG. 8 is a cross-sectional view of a dual lumen catheter with one antegrade valve and two retrograde valves.
Figure 7:
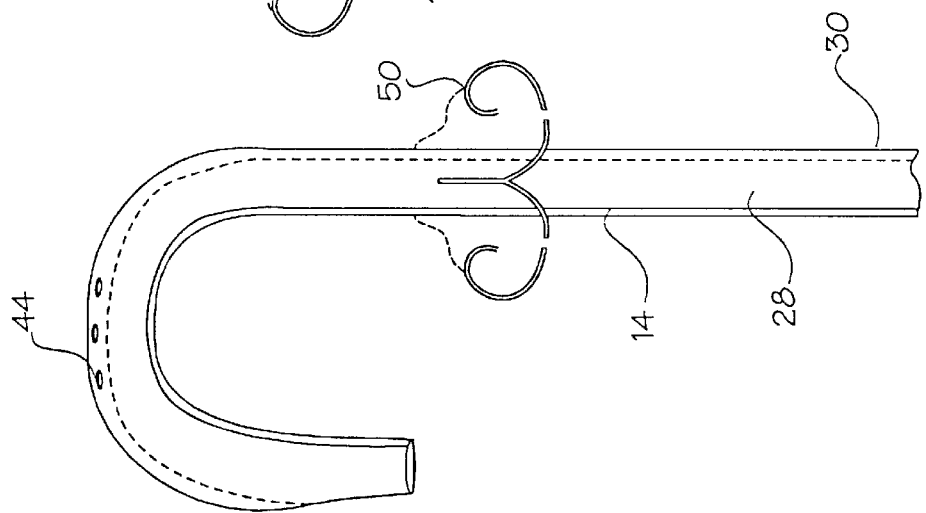
FIG. 7 is a cross-sectional view of a dual lumen catheter with a retrograde valve.

In FIG. 7 shows double lumen catheter 14 with a single retrograde valve 50 that is positioned downstream from directional side ports 44. In FIG. 8 double lumen catheter 14 includes one antegrade valve 42 and two retrograde valves 50 that are in fixed or moveable relationships to the exterior of double lumen catheter 14.

FIG. 9 illustrates a single lumen catheter 14 with a single antegrade valve 42 positioned upstream from directional side ports 44. The distal end of first lumen 28 may be opened or closed depending on the particular application.

FIG. 10 also illustrates a single lumen catheter 14 with a single retrograde valve 50 positioned downstream from directional side ports 44.

FIG. 11 illustrates a single lumen catheter 14 with one antegrade valve 42, one retrograde valve 50, and one inflatable balloon 52. Valve 50 and balloon 52 are each positioned downstream from antegrade valve 42.

Balloon 52 may be constructed of various materials and in various geometries. In one embodiment, balloon 52 has a collapsed profile small enough for introduction into the femoral or iliac artery, e.g., 4–9 mm outside diameter and an expanded (inflated) profile large enough to completely occlude the ascending aorta, e.g. 20–40 mm outside diameter. The ratio of expanded profile diameter to collapsed profile diameter will thus be between 2 and 10, and preferably between 5 and 10. Balloon 52 is further configured to maximize contact of the working surface of the balloon with the aortic wall to resist displacement and to minimize leakage around the balloon 52, preferably having a working surface with an axial length in the range of about 3 to about 7 cm when balloon 52 is expanded. Textural features such as ribs, ridges or bumps may also be provided on the balloon working surface for increased frictional effects to further resist displacement.

Figure 12:
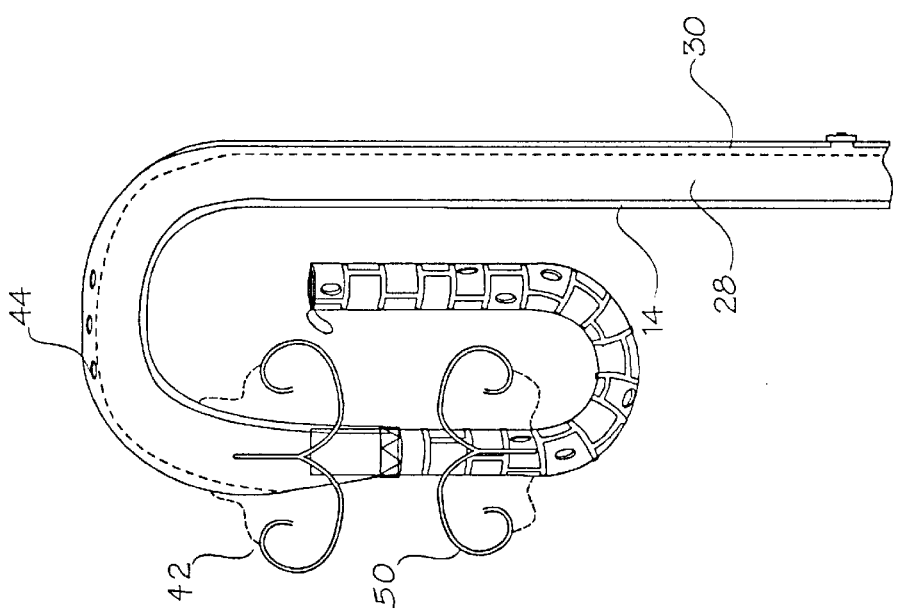
FIG. 12 is a cross-sectional view of a dual lumen catheter with an antegrade valve and a balloon positioned at a distal portion of the dual lumen catheter.

FIG. 12 illustrates a double lumen catheter 14 with an retrograde valve 50 positioned at a distal end of double lumen catheter 14, and a antegrade valve 42 positioned downstream from retrograde valve 50. Retrograde valve 50 is positioned below the aortic valve of the heart, and antegrade valve 42 is positioned above the aortic valve of the heart. Retrograde valve 50 is positioned at a distal end of double lumen catheter 14 or at an exterior surface of an extension member (not shown) which extends from the distal end of double lumen catheter 14. Double lumen catheter 14 may have a ring and strut construction which increases rigidity, minimizes kinking or coiling of double lumen catheter 14, or of a single lumen, triple lumen, and the like catheter 14.

Figure 13:
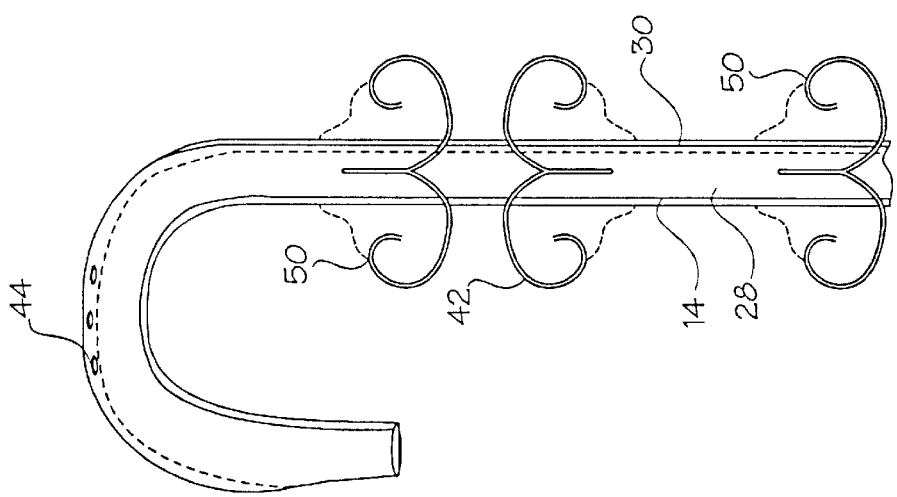
FIG. 13 is a cross-sectional view of a dual lumen catheter with an antegrade valve and two retrograde valve that are positioned at a non-distal portion of the dual lumen catheter.

FIG. 13 illustrates a double lumen catheter 14 with an antegrade valve 42 and two retrograde valve 50.

Figure 14:
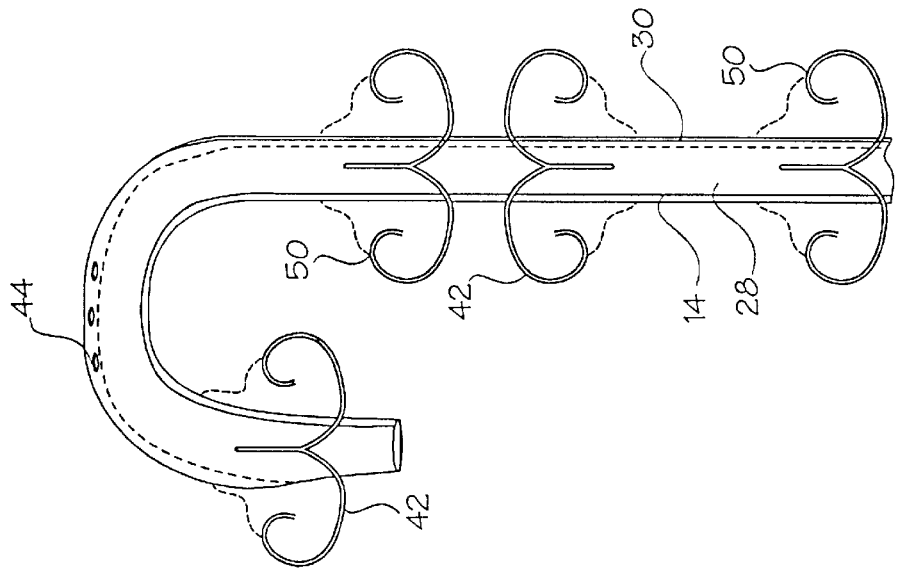
FIG. 14 is a cross-sectional view of a dual lumen catheter with two antegrade valves and two retrograde valves.

FIG. 14 illustrates a double lumen catheter 14 with two antegrade valves 42 and two retrograde valves 50.

Figure 17:
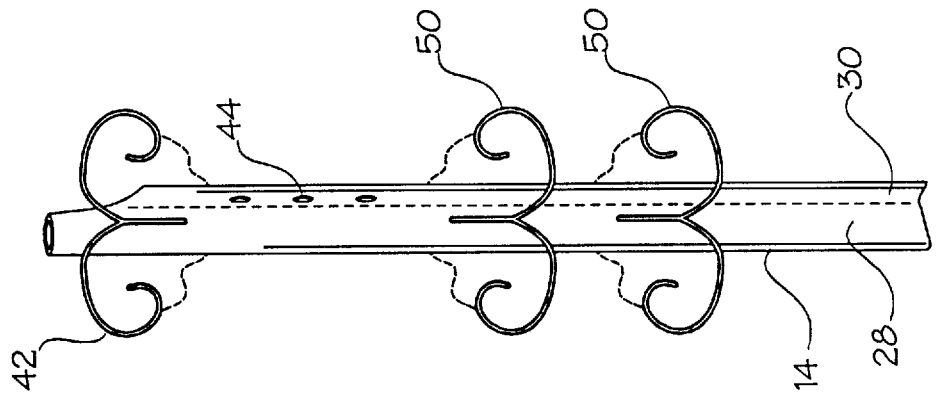
FIG. 17 is a cross-sectional view of a linear section of a dual lumen catheter with an antegrade valve and two retrograde valves.
Figure 16:
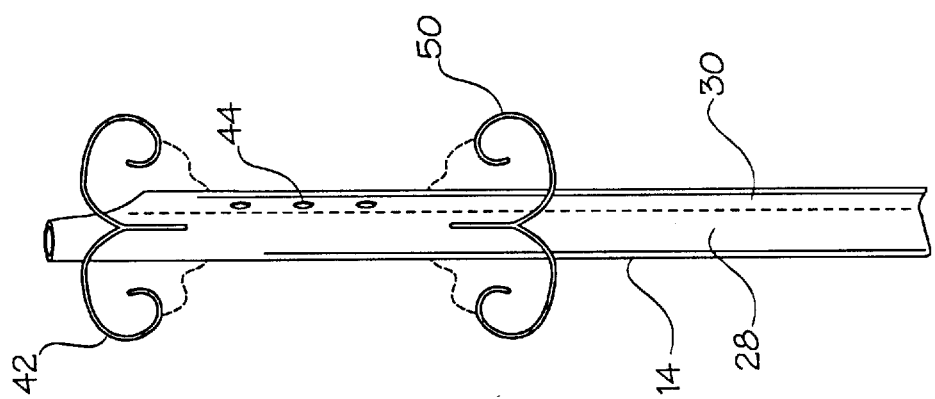
FIG. 16 is a cross-sectional view of a linear section of a dual lumen catheter with an antegrade valve and a retrograde valve.
Figure 15:
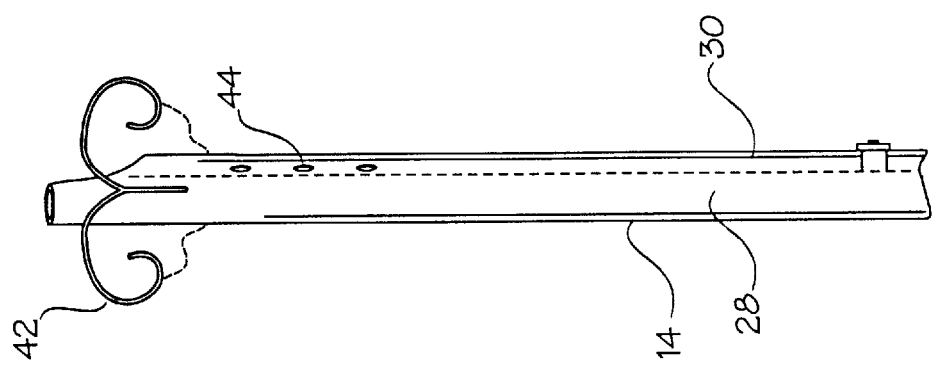
FIG. 15 is a cross-sectional view of a linear section of a dual lumen catheter with an antegrade valve.

FIGS. 15 through 17 illustrates a double lumen straight catheter 14, or a straight portion of catheter 14 with an antegrade valve 42 (FIG. 15), an antegrade valve 42 and a retrograde valve 50 (FIG. 16), a single antegrade valve 42 and two retrograde valves 50 (FIG. 17).

Figure 20:
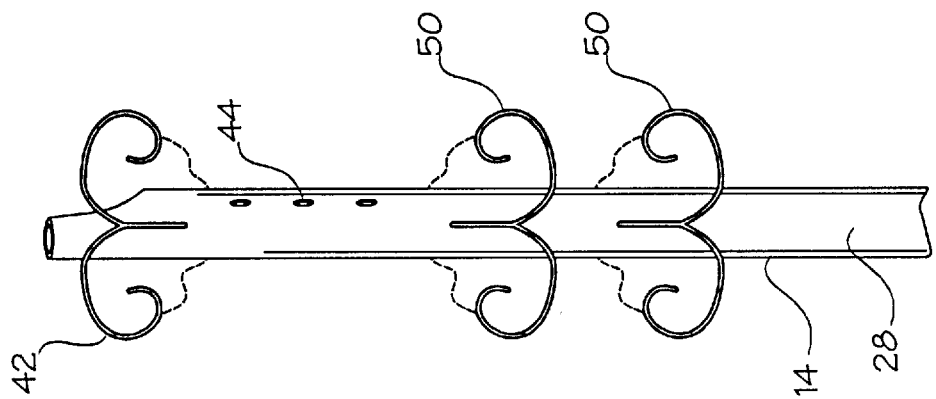
FIG. 20 is a cross-sectional view of a linear section of a single lumen catheter with an antegrade valve and two retrograde valves.
Figure 19:
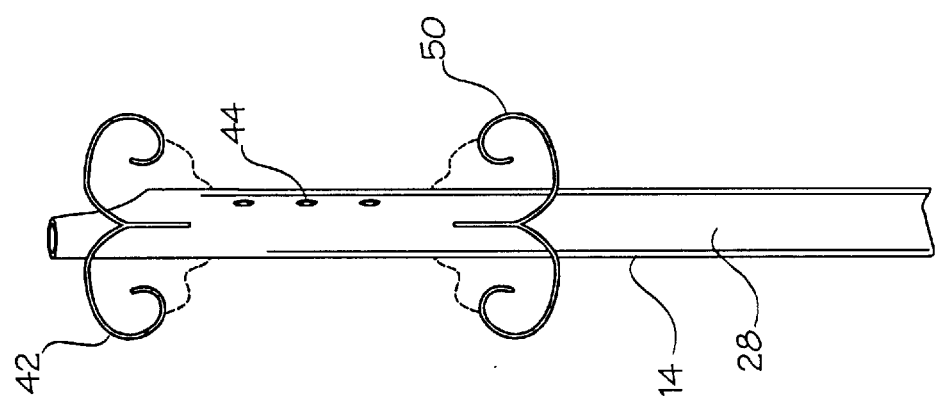
FIG. 19 is a cross-sectional view of a linear section of a single lumen catheter with an antegrade valve and a retrograde valve.
Figure 18:
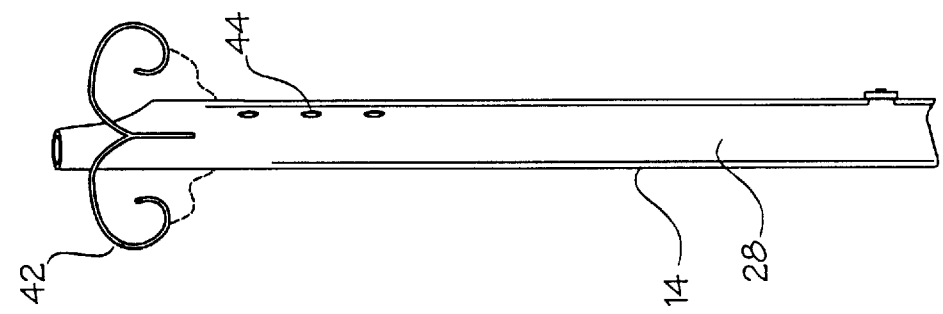
FIG. 18 is a cross-sectional view of a linear section of a single lumen catheter with an antegrade valve.

FIGS. 18 through 20 correspond to FIGS. 15 through 17 except that a single lumen catheter 14 is illustrated.

Figure 21:
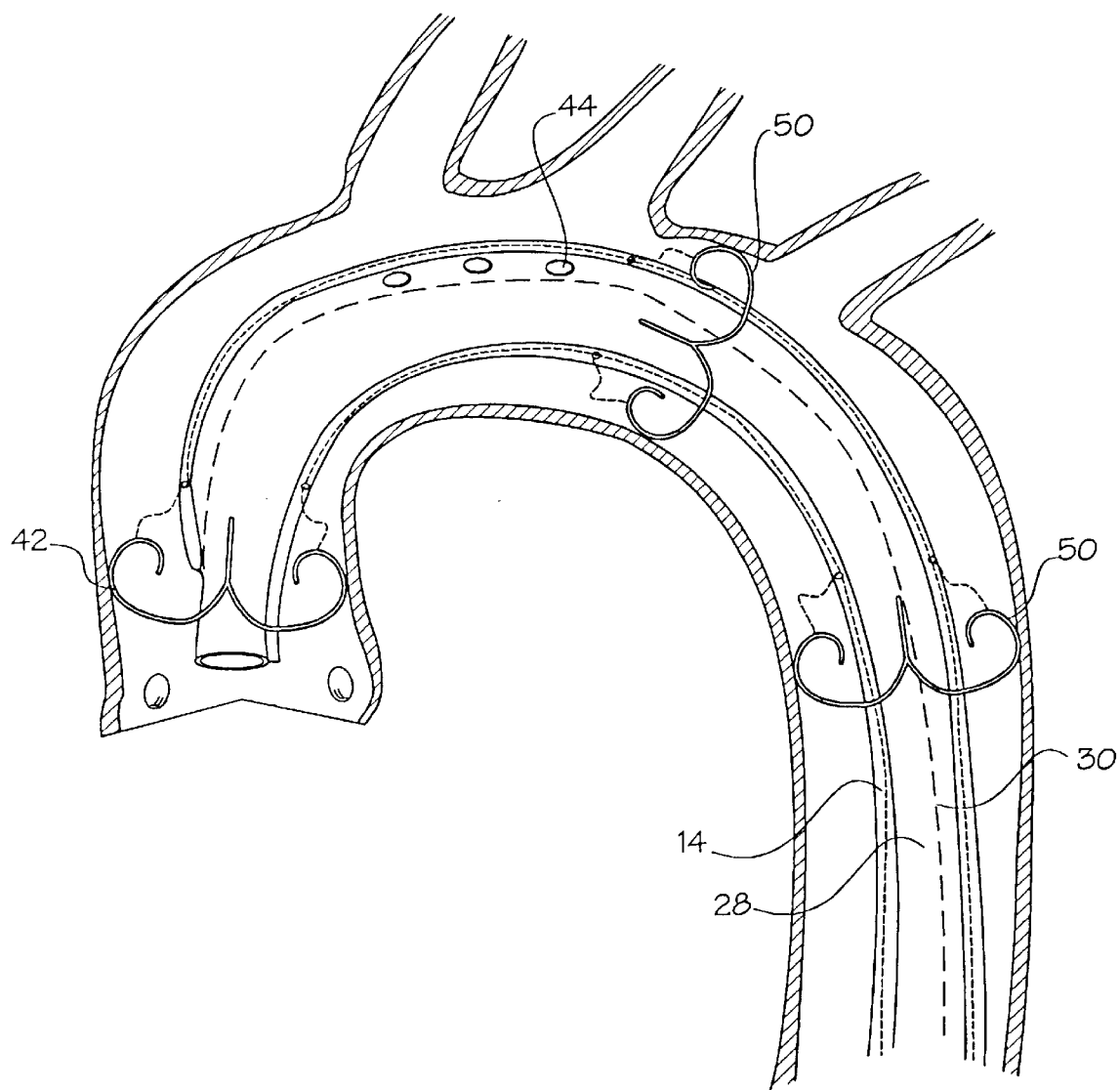
FIG. 21 is a cross-sectional view of a dual lumen catheter with an antegrade valve and two retrograde valves positioned in the aorta.

FIG. 21 illustrates a double lumen catheter 14 deployed in the aorta with a distal end terminating just above the aortic valve. A single antegrade valve 42, which is preferably a peripheral flow valve, is positioned downstream from the aortic valve. A first retrograde valve 50 is positioned downstream from the left carotid artery, and a second retrograde valve 50 positioned downstream from the left subclavian artery.

Figure 22:
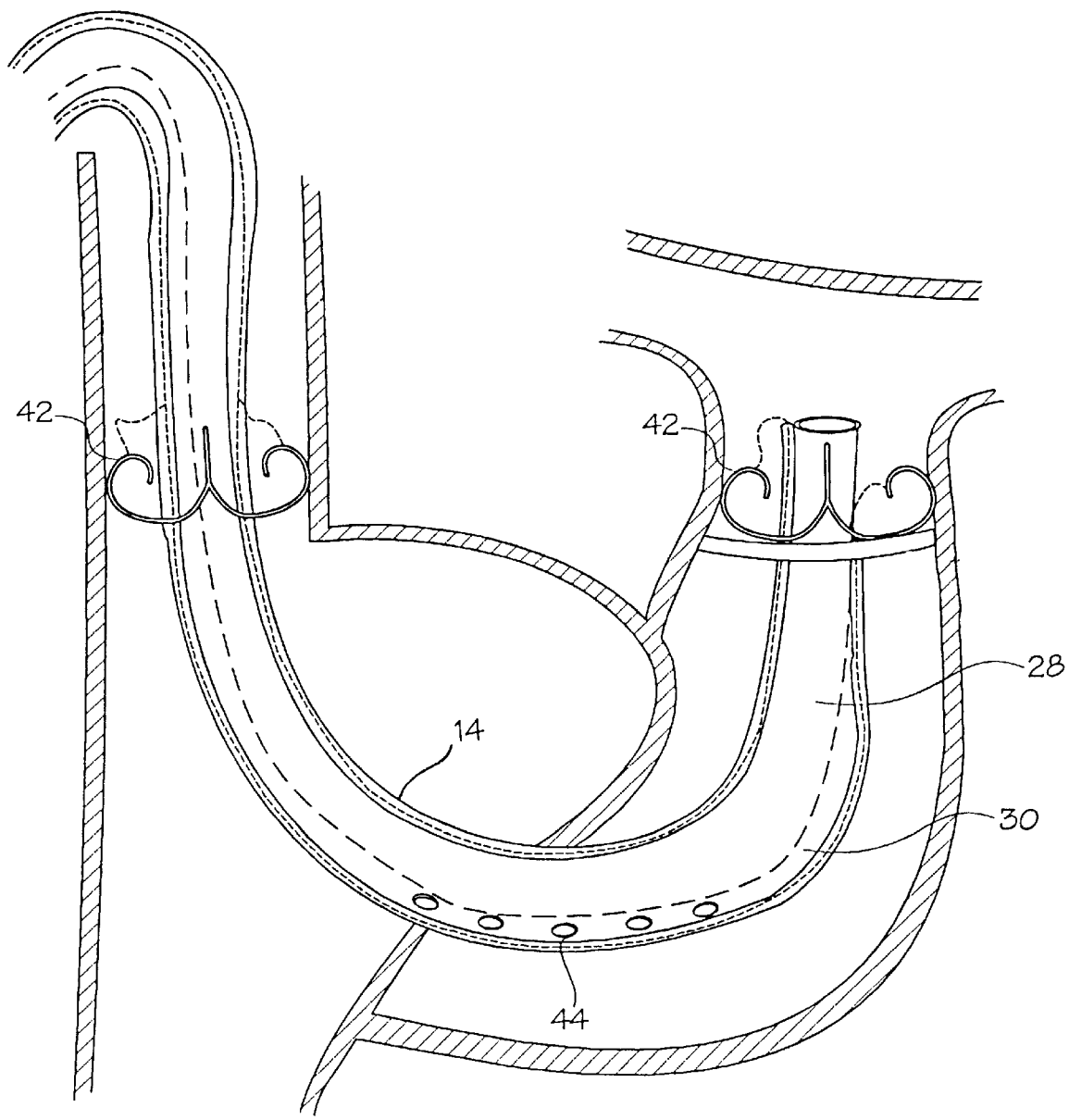
FIG. 22 is a cross-sectional view of a dual lumen catheter with two antegrade valves positioned in the right heart.

FIG. 22 illustrates a double lumen catheter 14 with first and second antegrade valves 42 deployed in the right heart. Double lumen catheter 14 enters the vein and traverses down the superior vena cava. Directional side ports 44 are configured to decompress the right atrium and the right ventricle. A distal tip of double lumen catheter 14 extends beyond the pulmonic valve. An antegrade valve 42 is positioned beyond the pulmonic valve.

Figure 23:
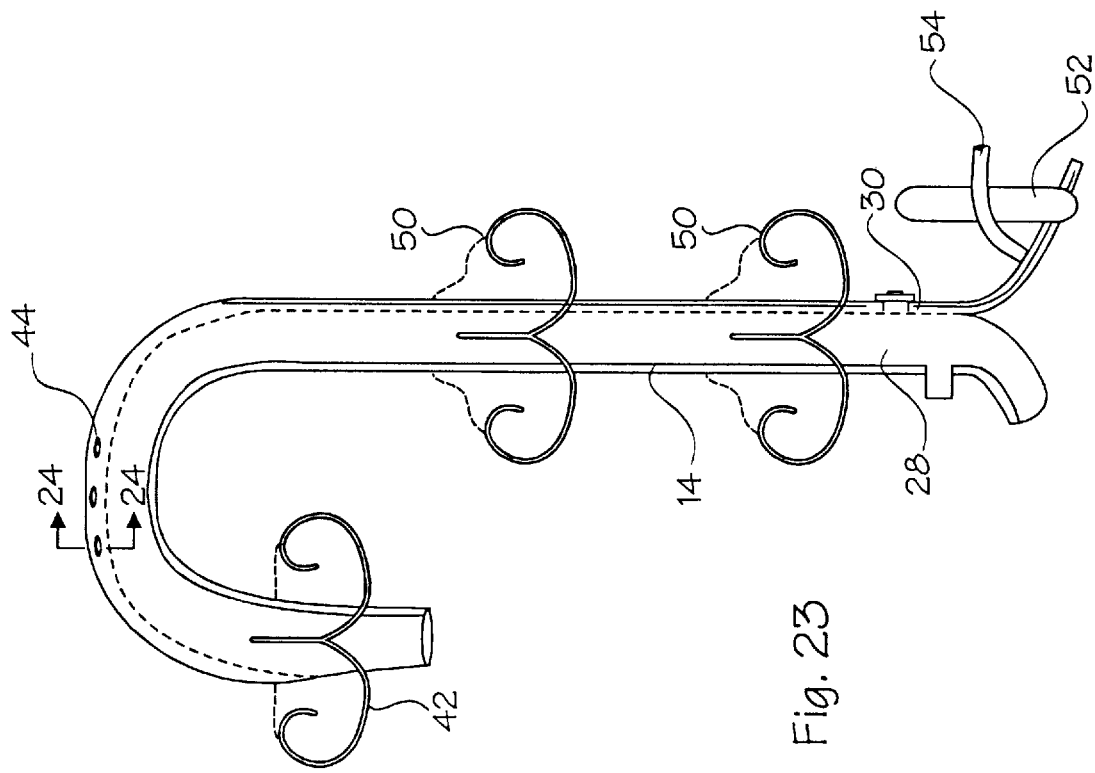
FIG. 23 is a cross-sectional view of a dual lumen catheter and a limb catheter.

FIG. 23 illustrates a double lumen catheter 14 with an antegrade valve 42, two retrograde valves 50 and a limb catheter 54. Limb catheter 54 perfuses or drains a blood vessel that is accessed peripherally. A balloon 52, or antegrade valve 42, is positioned at limb catheter 54.

Figure 24:
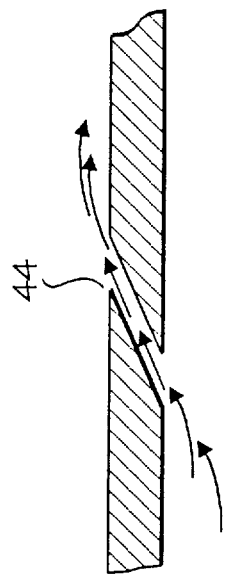
FIG. 24 is a cross-sectional view of the dual lumen catheter taken along the lines 24—24 of FIG. 23, illustrating the directional side ports.

FIG. 24 illustrates fluid flow from a directional side port 44 in a cross-sectional view.

Figure 25:
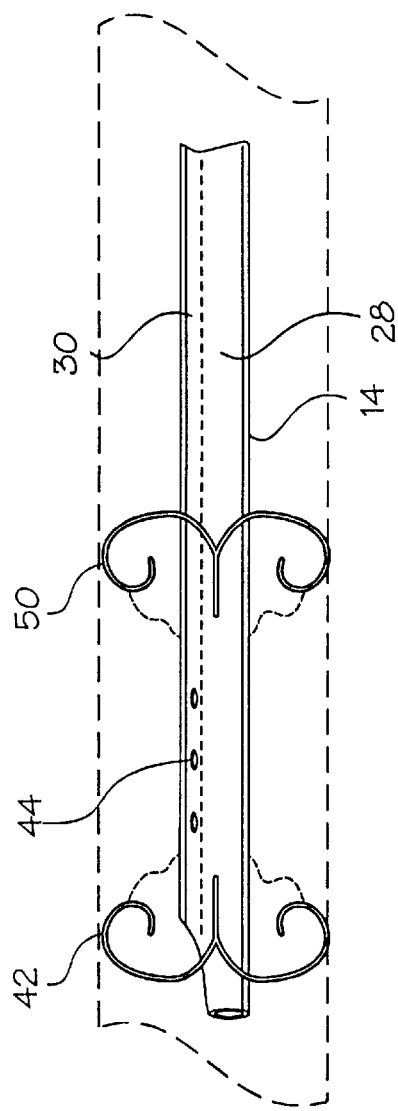
FIG. 25 is a cross-sectional view of a dual lumen catheter in a circulatory vessel illustrating antegrade and retrograde blood flow, blood flow through a second lumen of the dual lumen catheter and perfusion of an associated open vessel.

In FIG. 25 a double lumen catheter 14 is positioned in a circulatory (blood) vessel. Double lumen catheter 14 includes an antegrade valve 42, a retrograde valve 50, and side directional ports 44 positioned between valves 42 and 50. Antegrade blood flow through a distal end of double lumen catheter 14 perfuses blood back into second lumen 30 which is then ejected through the directional side ports 44 between the valves 42 and 50. In this manner blood is directed into the circulatory vessel in the vicinity of directional side ports 44. When a second vessel is positioned in the vicinity of directional side ports, the second vessel is perfused.

Figure 26A:
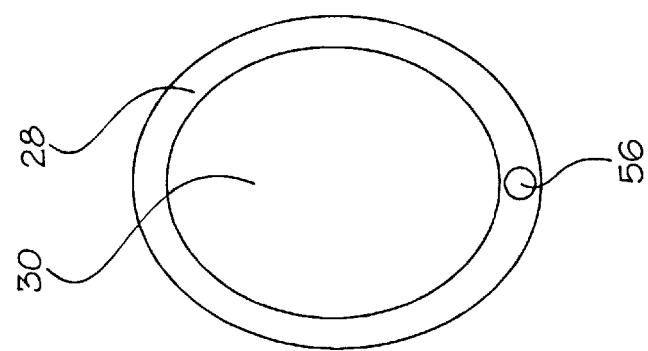
FIG. 26 is a cross-sectional view of the triple lumen catheter in a circulatory vessel.
Figure 26:
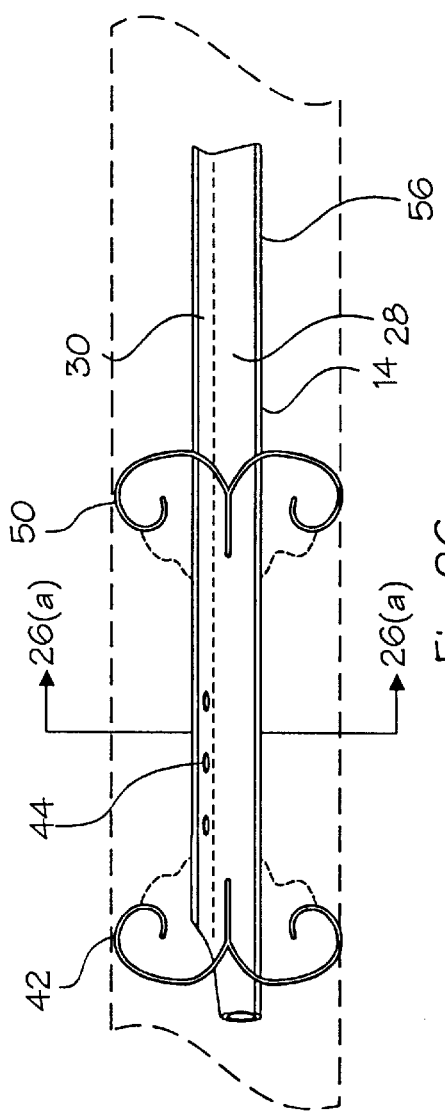

FIG. 26 illustrates a triple lumen catheter 14 positioned in a circulatory (blood) vessel and is similar to FIG. 25. Triple lumen catheter 14 includes first lumen 28, second lumen 30 and third lumen 56. An antegrade valve 42 and a retrograde valve 50 are included.

FIG. 26(a) illustrates a distal end of triple lumen catheter 14 at its distal end. Second lumen 30 and third lumen 56 can have open or closed distal ends. Second lumen 30 and third lumen 56 can each have a closed distal end and a port formed in a distal portion of a side wall of each respective lumen 30 and 56. FIGS. 26(b) through 26(d) illustrate various embodiments of the distal ends of dual and triple lumen catheters 14. Each of the first lumen 28, second lumen 30 and third lumen 56 may be configured with an open distal end 29 and/or with a side port 46.

Figure 27:
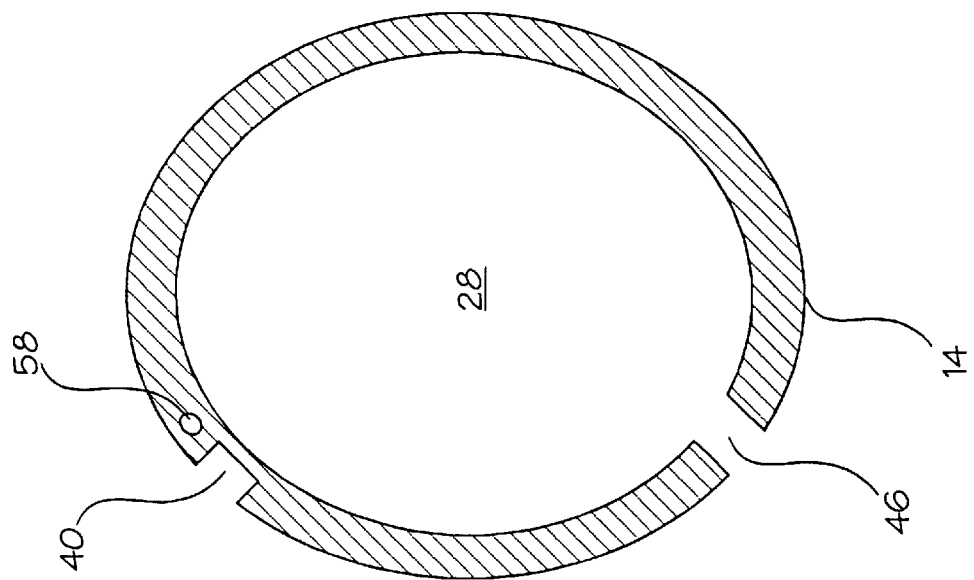
FIG. 27 is a cross-sectional view of a single lumen catheter with a track formed in a surface of the catheter body and a side port formed in the catheter body.

FIG. 27 illustrates a single lumen catheter 14 with an open third track 40 formed in a body structure of single lumen catheter 14. A single port 46 is formed in the body structure of single lumen catheter 14 and provides fluid communication between first lumen 28 and an exterior of single lumen catheter 14.

Figure 28:
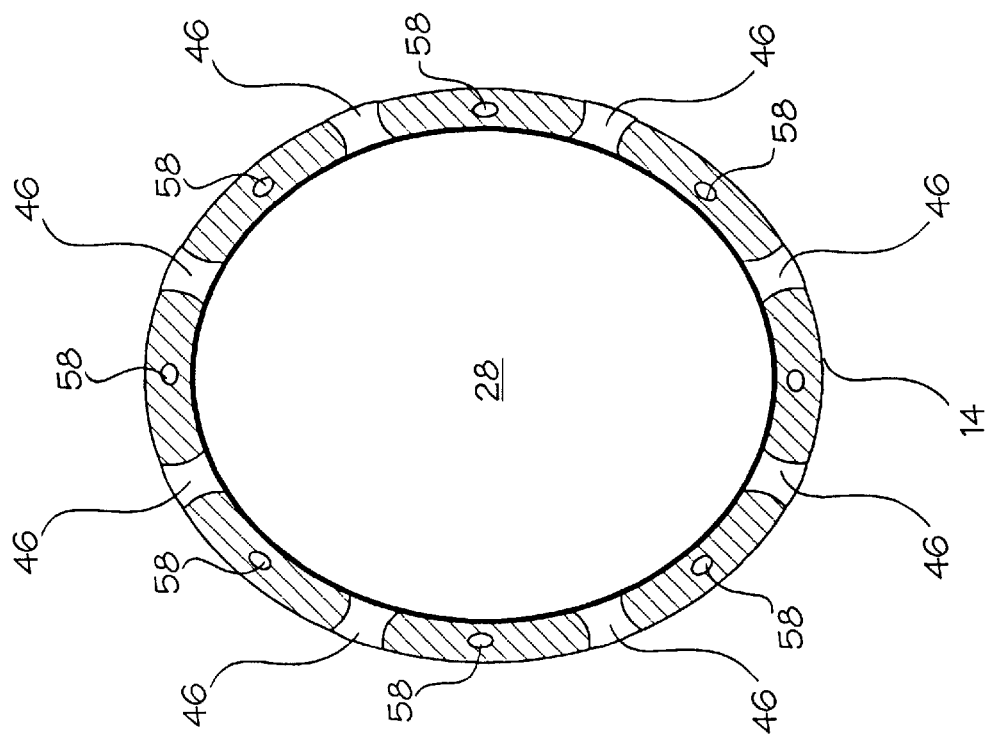
FIG. 28 is a cross-sectional view of a single lumen catheter with a track formed in a surface of the catheter body, multiple side ports formed in the catheter body, and multiple channels formed in the catheter body.

FIG. 28 illustrates a single lumen catheter 14 with an open third track 40 formed in a body structure of single lumen catheter 14. A plurality of side ports 46 and third channels 58 are formed in the body structure of single lumen catheter 14.

Figure 30:
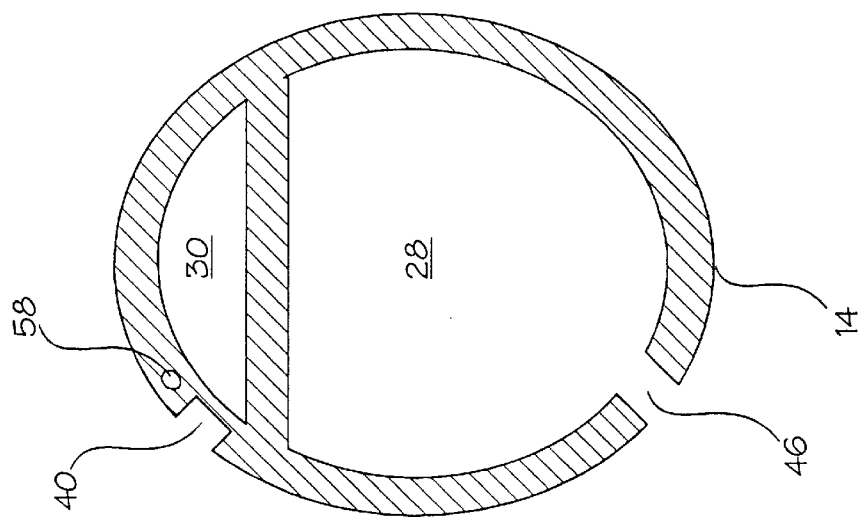
FIG. 30 is a cross-sectional view of a dual lumen catheter with a track and a port each formed in a side wall of a different lumen.
Figure 29:
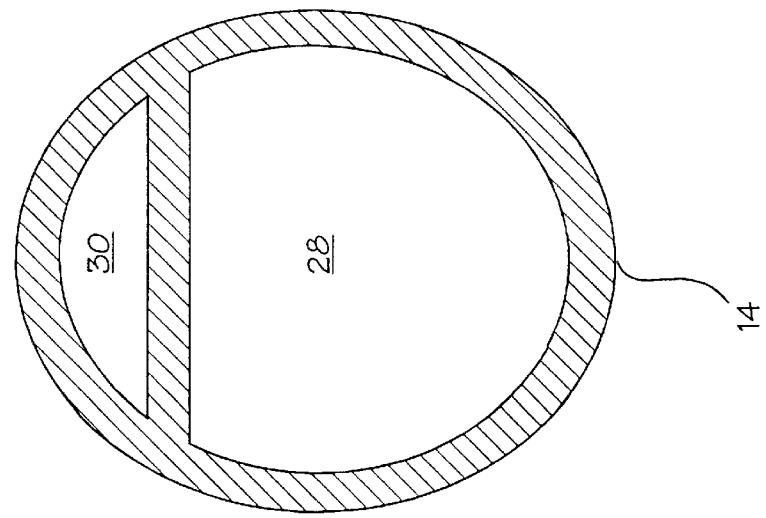
FIG. 29 is a cross-sectional view of a dual lumen catheter.

FIGS. 29 and 30 illustrate a double lumen catheter 14 where first lumen 28 and second lumen 30 occupy about 80% and 20%, respectively, of the effective working interior volume of double lumen catheter 14.

Figure 31:
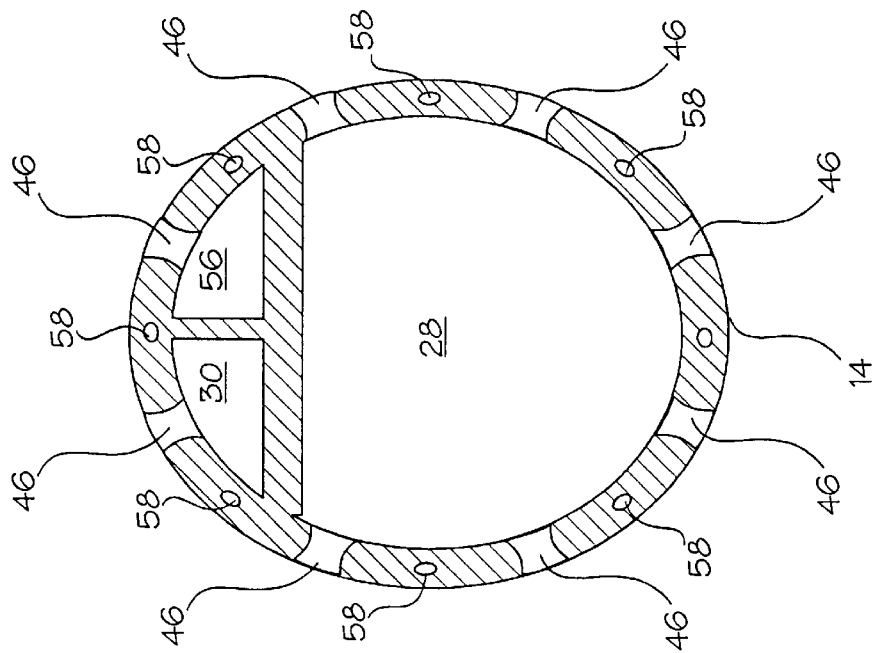
FIG. 31 is a cross-sectional view of a triple lumen catheter with multiple tracks, side ports and channels formed in the catheter body.

FIG. 31 illustrates a triple lumen catheter 14 where first lumen 28, second 30 and third lumen 56 occupy about 80%, 10% and 10%, respectively, of the effective working interior volume of triple lumen catheter 14. Preferably, first lumen 28, second 30 and third lumen 56 occupy about 20%, 70% and 10%, respectively, of the effective working interior volume of triple lumen catheter 14.

FIG. 32 illustrates a longitudinal cross-section view of a double lumen catheter 14 with an antegrade valve 42 and a retrograde valve 50. Directional side ports 44 are formed in a body structure of second lumen 30. One or more slidable members 48 are positioned on the exterior surface of double lumen catheter 14 to open and close directional side ports 44. A limb perfusion/drainage catheter 54 is coupled to first lumen 28. A blood pump/oxygenator port 60 extends from double lumen catheter 14 at a selected angle, e.g., 45 degrees, and is coupled to first lumen 28. Blood pump/oxygenator port 60 is coupled to a blood pump/oxygenator 62 which is also coupled to second lumen 30. A third track 40 provides for passing an advancement and retraction member 18, to direct opening and closing of leaflets 22, and pass valves or, surgical instruments, scopes, irrigation and aspiration cannulas and the like.

A dual diaphragm device 64 is coupled to a proximal end of first lumen 28. Dual diaphragm device 64 can also be coupled to multiple lumen catheters. Dual diaphragm device 64 includes a first fluid irrigation port 66, a second fluid irrigation port 68, a first diaphragm 70, second diaphragm 72 and instrument or device introduction chamber 73. Dual diaphragm device 64 provides an air lock to first lumen 28. This permits the introduction of different instruments and devices into first lumen 28. A balloon 52 is positioned around an exterior of double lumen catheter 14 and is coupled to an inflation and deflation port 74 configured to introduce and remove an inflation solution into and out of balloon 52.

Figure 33:
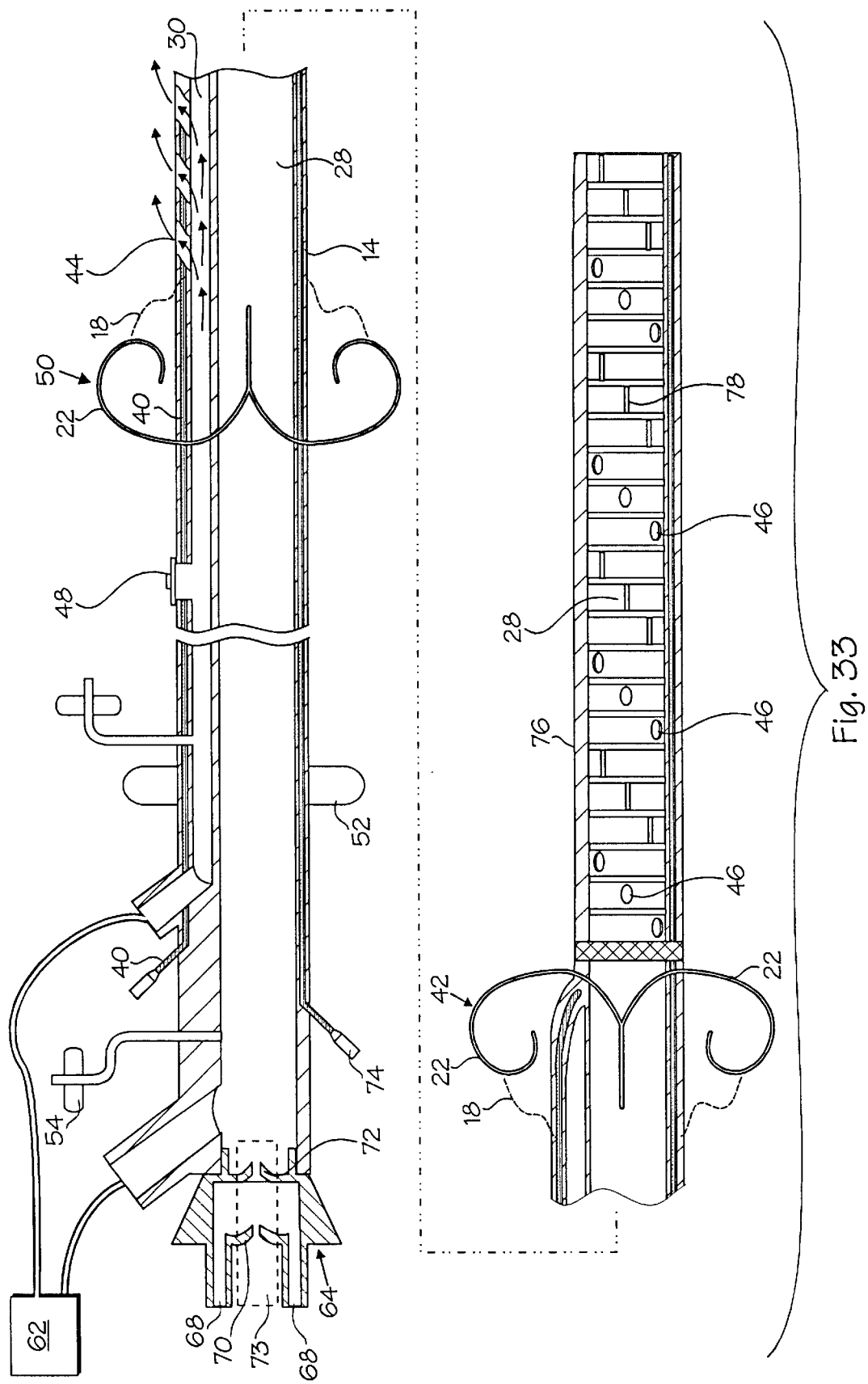
FIG. 33 is a cross-sectional view of a dual lumen catheter with a dual diaphragm device coupled to a proximal end of the dual lumen catheter, and a distal end with a plurality of rings, struts and ports.

FIG. 33 is similar to FIG. 32 except a plurality of rings 76 and struts 78 are formed in the distal portion of dual lumen catheter 14, providing a reinforced structure that is less subject to kinking and coiling. A plurality of side ports 46 may also be formed in the body of dual lumen catheter 14, in first lumen 28 and/or second lumen 30.

Figure 34:
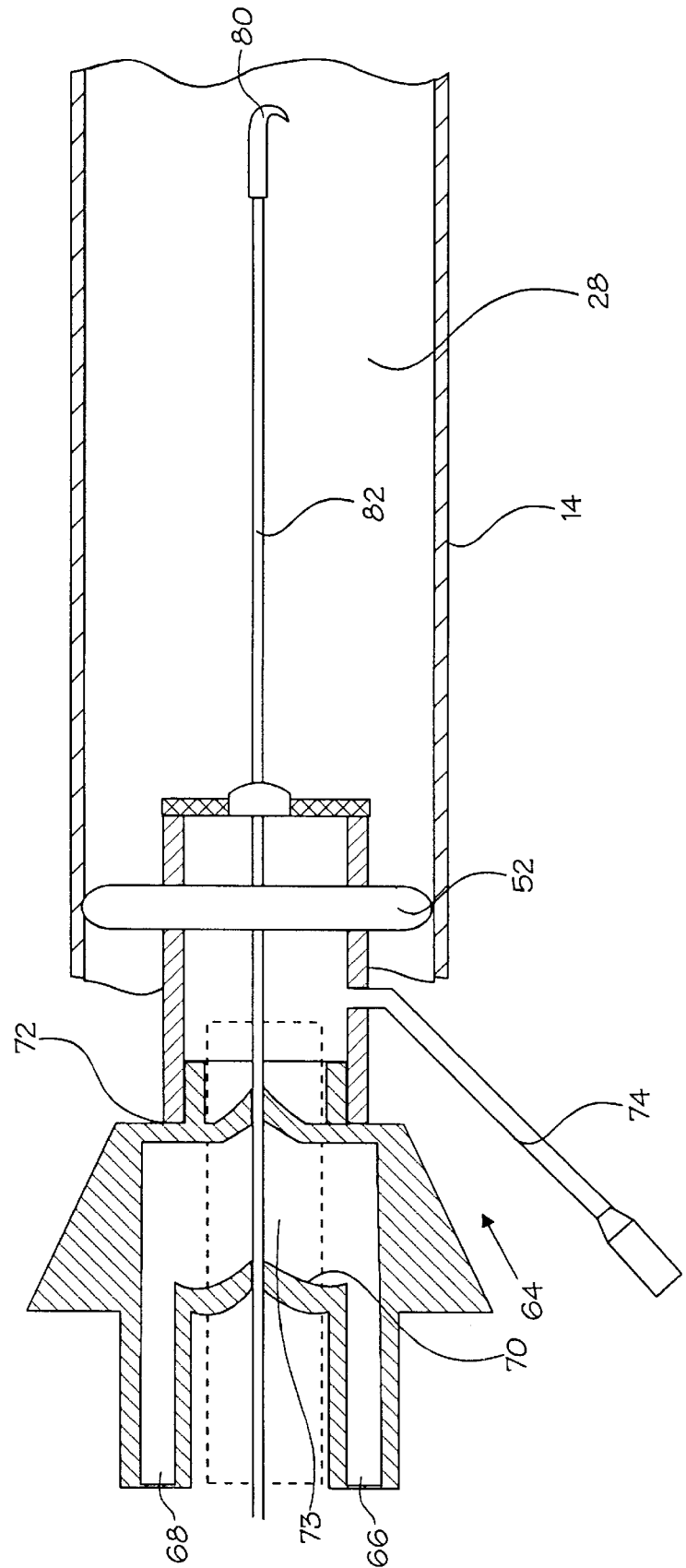
FIG. 34 is a cross-sectional view of a dual lumen catheter illustrating a dual diaphragm device, including its distal end.

Dual diaphragm device 64 is illustrated in FIG. 34. First fluid irrigation port 66 is a flush fluid inlet port, while second fluid irrigation port 68 is a flush fluid outlet port, providing fluid circulation. Dual diaphragm device 64 has a distal end that is geometrically configured to pierce a circulatory vessel, a heart chamber wall and access a mural wall of the heart. Alternatively, the distal end of dual diaphragm device 64 need not be very sharp and a blade member can be introduced out of distal end of dual diaphragm device 64. A guide wire 82 having a blade member 82 is shown extending beyond instrument introduction chamber 73.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A catheter device to regulate fluid flow within a circulatory vessel, comprising:
   an elongated catheter body configured to access one of a circulatory vessel or a heart chamber, the elongated catheter body including a proximal end, a distal end, and a first lumen including an open proximal end and a distal end with a port formed proximate the distal end of the first lumen; and
   an antegrade valve coupled to an exterior of the catheter body and configured to provide a controllable antegrade flow and a controllable retrograde flow along the exterior of the catheter body, wherein the antegrade valve includes one or more leaflets wherein the antegrade flow is greater than the retrograde flow.

2. The catheter device of claim 1, wherein the elongated catheter body includes a second lumen including an open proximal end and a distal end.

3. The catheter device of claim 2, wherein the antegrade valve includes a retraction connection point at a leaflet.

4. The catheter device of claim 2, wherein the second lumen includes a port formed at a distal portion of the distal end of the second lumen.

5. The catheter device of claim 2, where the second lumen includes a second lumen port formed in the catheter body at a distal portion of the distal end of the second lumen.

6. The catheter device of claim 1, wherein the elongated catheter body has a length of approximately 20 to 60 cm.

7. The catheter device of claim 1, wherein the antegrade valve is a central flow valve configured to provide a fluid flow through a center portion of the central flow valve and fluid flow traverses between the central flow valve and the catheter body.

8. The catheter device of claim 1, wherein the antegrade valve is a peripheral flow valve configured to provide the antegrade flow around an exterior of the leaflets and fluid flow traverses between the leaflets and a circulatory vessel wall.

9. The catheter device of claim 1, wherein the antegrade valve includes one or more retraction and advancement members coupled to the antegrade valve.

10. The catheter device of claim 1, further comprising:
    one or more unidirectional or bidirectional fluid flow fenestrations formed in the leaflets and configured to regulate the antegrade flow or the retrograde flow.

11. The catheter device of claim 1, wherein the antegrade valve is mounted at a fixed position on the exterior of the catheter body.

12. The catheter device of claim 1, wherein the antegrade valve is moveable along the exterior of the catheter body.

13. The catheter device of claim 1, wherein the antegrade valve includes a retraction connection point on a leaflet.

14. The catheter device of claim 1, wherein the antegrade valve includes two leaflets.

15. The catheter device of claim 1, wherein the antegrade valve is configured to be sufficiently retractable to provide a controllable antegrade and a controllable retrograde fluid flow past the antegrade valve.

16. The catheter device of claim 15, further comprising:

a retraction member coupled to the antegrade valve configured to provide retractable movement of the antegrade valve in a direction towards the catheter body.

17. The catheter device of claim 16, wherein the retraction member is coupled to an exterior surface of the catheter body.

18. The catheter device of claim 16, wherein the retraction member is positioned in an interior of the catheter body.

19. The catheter device of claim 16 wherein the retraction member is positioned in the first lumen of the catheter body.

20. The catheter device of claim 1, wherein the antegrade valve is configured to regulate fluid flow past the antegrade valve resulting from differential pressures on a first and a second side of the antegrade valve.

21. The catheter device of claim 20 further comprising:

one or more fenestrations formed in the catheter body and configured to provide a directional fluid flow.

22. The catheter device of claim 1, wherein the antegrade valve include one leaflet.

23. The catheter device of claim 1, wherein the antegrade valve includes two or more leaflets coupled to a retraction member.

24. The catheter device of claim 1, wherein the antegrade valve is configured to minimize a disruption of a lesion formed on an interior surface one of a vessel or a heart chamber.

25. The catheter device of claim 1, wherein the antegrade valve distal end is at least partially rounded.

26. The catheter device of claim 1, further comprising a side port formed in the catheter body, wherein the side port provides a directional flow of a fluid.

27. The catheter device of claim 26, further comprising a slidable member positioned adjacent to the side port and configured to open or close the side port and regulate fluid flow through the side port.

28. The catheter device of claim 1, wherein the elongated catheter body has a length of approximately 80 to 100 cm.

29. The catheter device of claim 1, wherein the elongated catheter body has a diameter of less than approximately 9 mm.

* * * * *

UNITED STATES PATENT AND TRADEMARK OFFICE
CERTIFICATE OF CORRECTION

PATENT NO. : 5,827,237
DATED : October 27, 1998
INVENTOR(S) : John A. Macoviak

It is certified that error appears in the above-identified patent and that said Letters Patent is hereby corrected as shown below:

Column 2, line 34 delete "co-pending application Ser. No." and insert --U.S. Patent No. 5,584,803 and U.S. Patent No. 5,370,685--;

Column 2, line 35 delete "07/991,188 and application Ser. No. 07/730,559";

Column 2, line 36 delete "assigned to the assignee of the present invention and are";

Column 2, line 37 delete "commonly";

Column 2, line 38 delete "assigned";

Column 2, line 38 delete "application Ser. No. 08/023,778 and insert --5,452,733--.

Signed and Sealed this

Eighth Day of February, 2000

*Attest:*

Q. TODD DICKINSON

*Attesting Officer*  *Commissioner of Patents and Trademarks*